US009789201B2

(12) United States Patent
Medina-Kauwe

(10) Patent No.: US 9,789,201 B2
(45) Date of Patent: Oct. 17, 2017

(54) SELF-ASSEMBLING COMPLEX FOR TARGETING CHEMICAL AGENTS TO CELLS

(71) Applicant: CEDARS-SINAI MEDICAL CENTER, Los Angeles, CA (US)

(72) Inventor: Lali K. Medina-Kauwe, Porter Ranch, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 11 days.

(21) Appl. No.: 14/796,758

(22) Filed: Jul. 10, 2015

(65) Prior Publication Data
US 2016/0008481 A1    Jan. 14, 2016

Related U.S. Application Data

(62) Division of application No. 12/667,436, filed as application No. PCT/US2008/069239 on Jul. 3, 2008, now Pat. No. 9,078,927.

(60) Provisional application No. 60/948,242, filed on Jul. 6, 2007.

(51) Int. Cl.
| A61K 47/48 | (2006.01) |
| C07K 14/47 | (2006.01) |
| A61K 49/00 | (2006.01) |
| A61K 31/704 | (2006.01) |
| C07K 14/475 | (2006.01) |
| A61K 47/61 | (2017.01) |
| A61K 47/64 | (2017.01) |
| A61K 38/03 | (2006.01) |
| A61K 38/08 | (2006.01) |

(52) U.S. Cl.
CPC ...... *A61K 47/48246* (2013.01); *A61K 31/704* (2013.01); *A61K 47/61* (2017.08); *A61K 47/64* (2017.08); *A61K 49/0056* (2013.01); *C07K 14/4756* (2013.01); *A61K 38/03* (2013.01); *A61K 38/08* (2013.01)

(58) Field of Classification Search
CPC ................. A61K 47/48246; C07K 14/4756
See application file for complete search history.

(56) References Cited

U.S. PATENT DOCUMENTS

| 5,559,099 | A | 9/1996 | Wickham et al. |
| 6,333,396 | B1 | 12/2001 | Filpula et al. |
| 9,078,927 | B2 | 7/2015 | Medina-Kauwe |
| 2003/0138432 | A1 | 7/2003 | Glazier |
| 2003/0170826 | A1 | 9/2003 | Rabinovich et al. |
| 2005/0042753 | A1 | 2/2005 | Yang et al. |
| 2005/0048606 | A1 | 3/2005 | Wang et al. |
| 2006/0014712 | A1 | 1/2006 | Neuman |
| 2006/0093674 | A1 | 5/2006 | Slobodkin et al. |
| 2008/0234183 | A1 | 9/2008 | Hallbrink et al. |
| 2009/0009441 | A1 | 1/2009 | Yamamoto et al. |
| 2010/0331273 | A1 | 12/2010 | Medina-Kauwe |
| 2011/0052697 | A1* | 3/2011 | Farokhzad ........... A61K 31/337 424/486 |
| 2012/0004181 | A1 | 1/2012 | Medina-Kauwe |
| 2014/0335025 | A1 | 11/2014 | Medina-Kauwe |
| 2015/0240231 | A1 | 8/2015 | Medina-Kauwe |
| 2016/0060316 | A1 | 3/2016 | Medina-Kauwe et al. |
| 2016/0331840 | A1 | 11/2016 | Medina-Kauwe |

FOREIGN PATENT DOCUMENTS

| WO | WO 02/062823 | * | 8/2002 |
| WO | WO-02/062823 A2 | | 8/2002 |
| WO | WO-02/094318 A1 | | 11/2002 |
| WO | WO 2007/137117 | * | 5/2007 |
| WO | WO-2007/137117 A2 | | 11/2007 |
| WO | WO-2009/009441 A3 | | 1/2009 |
| WO | WO-2010/085665 A2 | | 7/2010 |

OTHER PUBLICATIONS

Medina-Kauwe et al., 2001, Nonviral gene delivery to human breast cancer cells by targeted Ad5 penton proteins, Gene Therapy, 8: 1753-1761.*
A.E. Frankel et al., Targeted Toxins, Clin. Cancer Res., 6:326-334 (2000).
Agadjanian et al., Feb. 2006, Specific Delivery of Corroles to Cells via Noncovalent Conjugates with Viral Proteins, Pharmaceutical Research, 23(2): 367-377.
C.L. Vogel et al., Efficacy and safety of trastuzumab as a single agent in first-line treatment of HER2-overexpressing metastatic breast cancer, J. Clin. Oncol., 20:719-726 (2002), T. Kute et al., Cytometry, A57: (2004), abstract only.
Choudhury et al., Small interfering RNA (siRNA) inhibits the expression of the Her2/neu gene, upregulates HLA class I and induces apoptosis of Her2/neu positive tumor cell lines, (2004) International Journal of Cancer 108, 71-77.
D. Goren et al., Targeting of stealth liposomes to erbB-2 (Her/2) receptor: in vitro and in viv studies, Br. J. Cancer, 74:1749-1756 (1996).
D.J. Slamon et al., Use of Chemotherapy plus a monoclonal antibody against HER2 for metastatic breast cancer that overexpresses HER2, N. Engl. J. Med., 344:783-792 (2001).
Drummond et al., Optimizing liposomes for delivery of chemotherapeutic agents to solid tumors, Pharmacol. Rev., 51:691-743 (1999).

(Continued)

*Primary Examiner* — Amber D Steele
(74) *Attorney, Agent, or Firm* — Morrison & Foerster LLP

(57) ABSTRACT

The present invention relates to a complex that can be injected into the body to hone in on target cells to deliver molecules. In one embodiment, the invention provides a drug delivery system that includes components that self-assemble into one targeted conjugate. In another embodiment, the invention includes a targeted carrier protein and a nucleic acid sequence non-covalently linked to one or more drugs.

33 Claims, 29 Drawing Sheets

(56) References Cited

OTHER PUBLICATIONS

Faltus et al., Silencing of the HER2/neu gene by siRNA inhibits proliferation and induces apoptosis in HER2/neu-overexpressing breast cancer cells, (2004) Neoplasia 6, 786-795.
Fisher, K.J., and Wilson, J.M., The transmembrane domain of diphtheria toxin improves molecular conjugate gene transfer, (1997) Biochemical Journal 321, 49-58.
G. Minot et al., Anthracyclines: Molecular advances and pharmacologic developments in antitumor activity and cardiotoxicity, Pharmacol. Rev., 56:185-229 (2004).
G.R. Braslawsky et al., Antitumor Activity of Adriamycin (Hydrazone-linked) Immunoconjugates Compared with Free Adriamycin and Specificity of Tumor Cell Killing, Cancer Res., 50:6608-6614 (1990).
Goldman, R. et al. (1990). "Heterodimerization of the erbB- 1 and erbB-2 Receptors in Human Breast Carcinoma Cells: A Mechanism for Receptor Transregulation," *Biochemistry* 29(50):11024-11028.
J. Baselga et al., Phase II study of weekly intravenous recombinant humanized anti-p185HER2 monoclonal antibody in patients with HER2/neu-overexpressing metastatic breast cancer, J. Clin. Oncol., 14: (1996), abstract only.
K.A. Chester et al., Clinical applications of phage-derived sFvs and sFv fusion proteins, Disease Markers, 16: (2000), abstract only.
K.J. Fisher and J.M. Wilson, The transmembrane domain of diptheria toxin improves molecular conjugate gene transfer, Biochem. J., 321:49-58 (1997).
Kim et al., Interferon Induction by siRNA' and ssRNAs synthesized by phage polymerase, National Biotechnol., 2004, vol. 22(3), pp. 321-325.
L.K. Medina-Kauwe and X. Chen, Using GFP-ligand fusions to measure receptor-mediated endocytosis in living cellsVitamins and Hormones, journal = Vitamins and Hormones, vol. 65 (2002), abstract only.
L.K. Medina-Kauwe et al., Assessing the binding and endocytosis activity of cellular receptors using GFP-ligand fusions, BioTechniques, 29: (2000), abstract only.
M. Jeschke et al., Targeted inhibition of tumor-cell growth by recombinant heregulin-toxin fusion proteins, Intl. J. Cancer, 60: (1995), abstract only.
M. Schmidt et al., A suppression of metastasis formation by recombinant single chain antibody-toxin targeted to full-length and oncogenic variant EGF recprots, Oncogene, 18:1711-1721 (1999).
Medina-Kauwe et al., 3PO, a novel non-viral gene delivery system using engineered Ad5 penton proteins, (2001) Gene Therapy 8, 795-803.
Medina-Kauwe et al., Intracellular trafficking of nonviral vectors, (2005) Gene Ther 12, 1734-1751.
Medina-Kauwe, L.K. (Aug. 2002). "A Novel Gene Delivery System Targeted to Breast Cancer," Report by University of Southern California, Report Sponsored by U.S. Army Medical Research and Material Command, Fort Detrick, Maryland 21702-5012, fourteen pages.
P.A. Trail et al., Antigen-specific activity of carcinoma-reactive BR64-doxorubicin conjugates evaluated in vitro and in human tumor xenograft models, Cancer Res., 52:5693-5700 (1992).
P.A. Trail et al., Cure of xenografted human carcinomas by BR96-doxorubicin immunoconjugates, Science, 261: (1993), abstract only.
P.A. Trail et al., Monoclonal antibody drug immunoconjugates for targeted treatment of cancerCancer Immunol Immunother., 52: (2003), abstract only.
R. Glockshuber et al., A comparison of strategies to stabilize immunoglobin Fv-fragments, Biochem, 29: (1990), abstract only.
Rentsendorj, A. et al. (2006; e-published on Feb. 16, 2006). "Typical and Atypical Trafficking Pathways of Ad5 Penton Base Recombinant Protein: Implications for Gene Transfer," *Gene Therapy* 13:821-836.
Sepp-Lorenzino, L. et al. (Apr. 18, 1996). "Signal Transduction Pathways Induced by Heregulin in MDA-MB-453 Breast Cancer Cells," *Oncogene* 12(8):1679-1687.
Siwak et al., The Potential of Drug-carrying Immunoliposomes as Anticancer Agents, (2002) Clin. Cancer Res., 8: 955-956.
T. Kute et al., Development of herceptin resistance in breast cancer cells, Cytometry, A57:86-93 (2004)].
Zabner, J., Fasbender, A.J., Moninger, T., Poellinger, K.A., and Welsh, M.J., Cellular and molecular barriers to gene transfer by a cationic lipid, (1995) Journal of Biological Chemistry 270, 18997-19007.
PCT/US08/69239 International Report on Patentability dated Jan. 12, 2010, 9 pages.
PCT/US2010/021830 International Search Report and Written Opinion dated Jul. 15, 2010, 12 pages.
PCT/US2010/021830 International Preliminary Report on Patentability dated Jul. 26, 2011, 6 pages.
Agadjanian, H. et al. (Apr. 14-18, 2007). "Modified Viral Capsid Protein Mediates Non-Viral Targeting of Unique Non-Covalent Drug Conjugates to HER2+ Breast Cancer Cells," *Proceedings of the AACR Annual Meeting* 48:357, Abstract # 1505 (Abstract Only), 2 pages.
Baselga, J. et al. (Mar. 1996). "Phase II Study of Weekly Intravenous Recombinant Humanized Anti-p185$^{HER2}$ Monoclonal Antibody in Patients with HER2/neu-Overexpressing Metastatic Breast Cancer," *J. Clin. Oncol.* 14(3):737-744.
Chester, K.A. et al. (2000). "Clinical Applications of Phage-Derived sFvs and sFv Fusion Proteins," *Disease Markers* 16(1-2):53-62.
Cobleigh, M.A. et al. (1998). "Efficacy and Safety of Herceptin™ (Humanized Anti-HER2 Antibody) as a Single Agent in 222 Women with HER2 Overexpression Who Relapsed Following Chemotherapy for Metastatic Breast Cancer," *376 Proc. Am. Soc. Clin. Oncol.* 17:97a, 3 pages.
Denny, W.A. (1989). "DNA-Intercalating Ligands as Anti-Cancer Drugs:Prospects for Future Design," *Anticancer Drugs Des.* 4(4):241-263.
Glockshuber, R. et al. (Feb. 1990). "A Comparison of Strategies to Stabilize Immunoglobin $F_v$-Fragments," *Biochem.* 29(6):1362-1367.
International Preliminary Report of Patentablity for PCT/US2008/69239 dated Jan. 12, 2010 and filed on Jul. 3, 2008, 9 pages.
International Search Report for PCT/US2008/69239 dated Jan. 28, 2009 and filed on Jul. 3, 2008, 3 pages.
Jeschke, M. et al. (Mar. 3, 1995). "Targeted Inhibition of Tumor-Cell Growth by Recombinant Heregulin-Toxin Fusion Proteins," *Intl. J. Cancer* 60(5):730-739.
Medina-Kauwe, L.K.et al. (Sep. 2000). "Assessing the Binding and Endocytosis Activity of Cellular Receptors Using GFP-Ligand Fusions," *BioTechniques* 29(3):602-609.
Medina-Kauwe, L.K. et al. (2002). "Using GFP-Ligand Fusions to Measure Receptor-Mediated Endocytosis in Living Cells," *Vitamins and Hormones* 65:81-95.
Medina-Kauwe (Jun. 2007). "Targeting siRNA Missiles to Her2+ Breast Cancer," retrieved from <http://www.dtic.mil/cgi-bin/GetTRDoc?AD=ADA472023>, lasted visited Jun. 21, 2017, (13 pages).
Medina-Kauwe (2008). "Targeting siRNA Missiles to Her2+ Breast Cancer", *U.S. Army Medical Research and Material Command Fort Detrick*, Maryland, (10 pages).
Park, J.W. et al. (2002). "Anti-HER2 Immunoliposomes: Enhanced Efficacy Attributable to Targeted Delivery," *Clin. Cancer Res.* 8:1172-1181.
Sliwkowski et al. (May 20, 1994). "Coexpression of *erb*B2 and *erb*B3 proteins Reconstitutes a High Affinity Receptor for Heregulin," *Journal of Biological Chemistry* 269(20):14661-14665.
Trail, P.A. et al. (Jul. 9, 1993). "Cure of Xenografted Human Carcinomas by BR96-Doxorubicin Immunoconjugates," *Science* 261(5118):212-215.
Trail, P.A.et al. (May 2003). "Monoclonal Antibody Drug Immunoconjugates for Targeted Treatment of Cancer," *Cancer Immunol Immunother.* 52(5):328-337, (e-pub. Jan. 16, 2003).

(56) References Cited

OTHER PUBLICATIONS

Vogel, C.L. et al. (Feb. 1, 2002). "Efficacy and Safety of Trastuzumab as a Single Agent in First-Line Treatment of *HER2*-Overexpressing Metastatic Breast Cancer," *J. Clin. Oncol.* 20(3):719-726.

Written Opinion of International Search Authority for PCT/US2008/69239 dated Jan. 28, 2009 and filed on Jul. 3, 2008.

Year of Publication retrieved from <http://rep945.infoeach.com/view-OTQ1fDgzNDY1NQ==.html>, last visited on Jun. 21, 2017, 1 page.

Medina-Kauwe, L.K. et al. (Aug. 24-29, 1997). "A Novel Gene Delivery System for Cell-Specific Targeting," *Faseb Journal*, 11(9):A862, Meeting: 17th International Congress of Biochemistry and Molecular Biology in conjunction with the Annual Meeting of the American Society for Biochemistry and Molecular Biology, San Francisco, CA. Abstract Only.

Medina-Kauwe, L.K. et al. (Nov. 2002). Ad5 Capsid Protein Uptake and Trafficking in HeLa Cells. *Molecular Biology of the Cell*, 13(Supplement):541a-542a, Abstract No. 3051, Meeting: 42nd Annual Meeting of the American Society for Cell Biology. San Francisco, CA, USA. American Society for Cell Biology.

Medina-Kauwe, L.K. (Nov. 14, 2003). "Endocytosis of Adenovirus and Adenovirus Capsid Proteins," *Adv. Drug Delivery Rev.* 55(11):1485-1496.

Medina-Kauwe, L.K. (2003). "Heregulin-Targeted Protein Uptake for Breast Cancer," NCI: 1R01CA102126-01, Abstract Only, 4 pages.

Medina-Kauwe, L.K. (2004). "Heregulin-Targeted Protein Uptake for Breast Cancer," NCI: 5R01CA102126-02, Abstract Only, 4 pages.

Medina-Kauwe, L.K. (2005). "Heregulin-Targeted Protein Uptake for Breast Cancer," NCI: 5R01CA102126-03, Abstract Only, 4 pages.

Medina-Kauwe, L.K. (2006). "Heregulin-Targeted Protein Uptake for Breast Cancer," NCI: 5R01CA102126-04, Abstract Only, 4 pages.

Medina-Kauwe, L.K. (2005). "Introduction to the Special Issue: Traveling the Intracellular Highway to Gene Therapy," *Gene Therapy* 12(11):863-864.

Medina-Kauwe, L.K. (2006). "Non-Viral Mediated Gene Delivery for Therapeutic Applications," Chapter 8 in *Gene Therapy for Neurological Disorders*, 115-140.

Medina-Kauwe, L.K. (2007). "A Novel Targeted Therapeutic Using Viral Capsid Protein," NCI: 1R21CA116014-01A2, Abstract Only, 4 pages.

Medina-Kauwe, L.K. (2008). "A Novel Targeted Therapeutic Using Viral Capsid Protein," NCI: 5R21CA116014-02, Abstract Only, 4 pages.

U.S. Appl. No. 15/624,228, filed Jun. 15, 2017 (Copy not attached).

* cited by examiner

Brightfield      GFP      Merged

Secondary Ab Only     HER2     HER3     HER4

SEQUENCE LISTING

```
<160> NUMBER OF SEQ ID NOS: 12

<210> SEQ ID NO 1
<211> LENGTH: 33
<212> TYPE: DNA
<213> ORGANISM: Homo sapiens

<400> SEQUENCE: 1
gcatcagaat tctcaaaaag tgcggctcga tag                              33

<210> SEQ ID NO 2
<211> LENGTH: 60
<212> TYPE: DNA
<213> ORGANISM: Homo sapiens

<400> SEQUENCE: 2
catgaattca tttttttttt tttttttttt tttttttttt aaaagtgcgg ctcgatagga   60
```

<210> SEQ ID NO 3
<211> LENGTH: 63
<212> TYPE: DNA
<213> ORGANISM: Homo sapiens

<400> SEQUENCE: 3

| | | | | | |
|---|---|---|---|---|---|
| atgaattcat | tttttttttt | tttttttttt | tttttttta | gatctacttc | caccacttcc | 60 |
| acc | | | | | | 63 |

<210> SEQ ID NO 4
<211> LENGTH: 2382
<212> TYPE: DNA
<213> ORGANISM: Homo sapiens

<400> SEQUENCE: 4

| | | | | | |
|---|---|---|---|---|---|
| ttgcctcccc | gattgaaaga | gatgaaaagc | caggaatcgg | ctgcaggttc | caaactagtc | 60 |
| cttcggtgtg | aaaccagttc | tgaatactcc | tctctcagat | tcaagtggtt | caagaatggg | 120 |
| aatgaattga | atcgaaaaaa | caaaccacaa | aatatcaaga | tacaaaaaaa | gccagggaag | 180 |
| tcagaacttc | gcattaacaa | agcatcactg | gctgattctg | gagagtatat | gtgcaaagtg | 240 |
| atcagcaaat | taggaaatga | cagtgcctct | gccaatatca | ccatcgtgga | atcaaacgag | 300 |
| atcatcactg | gtatgccagc | ctcaactgaa | ggagcatatg | tgtcttcaga | gtctcccatt | 360 |
| agaatatcag | tatccacaga | aggagcaaat | acttcttcat | ctacatctac | atccaccact | 420 |
| gggacaagcc | atcttgtaaa | atgtgcggag | aaggagaaaa | cttctgtgt | gaatggaggg | 480 |
| gagtgcttca | tggtgaaaga | cctttcaaac | ccctcgagat | acttgtgcaa | gtgccaacct | 540 |
| ggattcactg | gagcaagatg | tactgagaat | gtgcccatga | agtccaaaa | ccaagaaaag | 600 |
| gcggaggagc | tgtacggtgg | aagtggtgga | agtggatcca | tgcggcgcgc | ggcgatgtat | 660 |
| gaggaaggtc | ctcctccctc | ctacgagagt | gtggtgagcg | cggcgccagt | ggcggcggcg | 720 |
| ctgggttctc | ccttcgatgc | tccctggac | ccgccgtttg | tgcctccgcg | gtacctgcgg | 780 |
| cctaccgggg | ggagaaacag | catccgttac | tctgagttgg | caccctatt | cgacaccacc | 840 |
| cgtgtgtacc | tggtggacaa | caagtcaacg | gatgtggcat | ccctgaacta | ccagaacgac | 900 |
| cacagcaact | ttctgaccac | ggtcattcaa | acaatgact | acagcccggg | ggaggcaagc | 960 |
| acacagacca | tcaatcttga | cgaccggtcg | cactggggcg | cgacctgaa | aaccatcctg | 1020 |
| cataccaaca | tgccaaatgt | gaacgagttc | atgtttacca | ataagtttaa | ggcgcgggtg | 1080 |
| atggtgtcgc | gcttgcctac | taaggacaat | caggtggagc | tgaaatacga | gtgggtggag | 1140 |
| ttcacgctgc | ccgagggcaa | ctactccgag | accatgacca | tagaccttat | gaacaacgcg | 1200 |
| atcgtggagc | actacttgaa | agtgggcaga | cagaacgggg | ttctggaaag | cgacatcggg | 1260 |
| gtaaagtttg | acacccgcaa | cttcagactg | gggtttgacc | ccgtcactgg | tcttgtcatg | 1320 |
| cctgggggtat | atacaaacga | agccttccat | ccagacatca | ttttgctgcc | aggatgcggg | 1380 |
| gtggacttca | cccacagccg | cctgagcaac | ttgttgggca | tccgcaagcg | gcaacccttc | 1440 |
| caggagggct | ttaggatcac | ctacgatgat | ctggagggtg | gtaacattcc | cgcactgttg | 1500 |
| gatgtggacg | cctaccaggc | gagcttgaaa | gatgacaccg | aacagggcgg | gggtggcgca | 1560 |
| ggcggcagca | acagcagtgg | cagcggcgcg | aagagaact | ccaacgcggc | agccgcggca | 1620 |
| atgcagccgg | tggaggacat | gaacgatcat | gccattcgcg | cgacaccttt | gccacacgg | 1680 |
| gctgaggaga | agcgcgctga | ggccgaagca | gcggccgaag | ctgccgcccc | cgctgcgcaa | 1740 |

| | |
|---|---:|
| cccgaggtcg agaagcctca gaagaaaccg gtgatcaaac ccctgacaga ggacagcaag | 1800 |
| aaacgcagtt acaacctaat aagcaatgac agcaccttca cccagtaccg cagctggtac | 1860 |
| cttgcataca actacggcga ccctcagacc ggaatccgct catggaccct gctttgcact | 1920 |
| cctgacgtaa cctgcggctc ggagcaggtc tactggtcgt tgccagacat gatgcaagac | 1980 |
| cccgtgacct tccgctccac gcgccagatc agcaactttc cggtggtggg cgccgagctg | 2040 |
| ttgcccgtgc actccaagag cttctacaac gaccaggccg tctactccca actcatccgc | 2100 |
| cagtttacct ctctgaccca cgtgttcaat cgctttcccg agaaccagat tttggcgcgc | 2160 |
| ccgccagccc ccaccatcac caccgtcagt gaaaacgttc ctgctctcac agatcacggg | 2220 |
| acgctaccgc tgcgcaacag catcggagga gtccagcgag tgaccattac tgacgccaga | 2280 |
| cgccgcacct gcccctacgt ttacaaggcc ctgggcatag tctcgccgcg cgtcctatcg | 2340 |
| agccgcactt ttaaaaaaaa aaaaaaaaaa aaaaaaaaaa aa | 2382 |

<210> SEQ ID NO 5
<211> LENGTH: 2382
<212> TYPE: DNA
<213> ORGANISM: Homo sapiens

<400> SEQUENCE: 5

| | |
|---|---:|
| tttttttttt tttttttttt tttttttttt aaaagtgcgg ctcgatagga cgcgcggcga | 60 |
| gactatgccc agggccttgt aaacgtaggg gcaggtgcgg cgtctggcgt cagtaatggt | 120 |
| cactcgctgg actcctccga tgctgttgcg cagcggtagc gtcccgtgat ctgtgagagc | 180 |
| aggaacgttt tcactgacgg tggtgatggt ggggctggc gggcgcgcca aaatctggtt | 240 |
| ctcgggaaag cgattgaaca cgtgggtcag agaggtaaac tggcggatga gttgggagta | 300 |
| gacggcctgg tcgttgtaga agctcttgga gtgcacgggc aacagctcgg cgcccaccac | 360 |
| cggaaagttg ctgatctggc gcgtggagcg aaggtcacg gggtcttgca tcatgtctgg | 420 |
| caacgaccag tagacctgct ccgagccgca ggttacgtca ggagtgcaaa gcagggtcca | 480 |
| tgagcggatt ccggtctgag ggtcgccgta gttgtatgca aggtaccagc tgcggtactg | 540 |
| ggtgaaggtg ctgtcattgc ttattaggtt gtaactgcgt tcttgctgt cctctgtcag | 600 |
| gggtttgatc accggtttct tctgaggctt ctcgacctcg ggttgcgcag cggggcggc | 660 |
| agcttcggcc gctgcttcgg cctcagcgcg cttctcctca gcccgtgtgg caaaggtgtc | 720 |
| gccgcgaatg gcatgatcgt tcatgtcctc caccggctgc attgccgcgg ctgccgcgtt | 780 |
| ggagttctct tccgcgccgc tgccactgct gttgctgccg cctgcgccac ccccgccctg | 840 |
| ttcggtgtca tctttcaagc tcgcctggta ggcgtccaca tccaacagtg cgggaatgtt | 900 |
| accaccctcc agatcatcgt aggtgatcct aaagccctcc tggaagggtt gccgcttgcg | 960 |
| gatgcccaac aagttgctca gcggctgtg ggtgaagtcc accccgcatc ctggcagcaa | 1020 |
| aatgatgtct ggatggaagg cttcgttttgt atataccccca ggcatgacaa gaccagtgac | 1080 |
| ggggtcaaac cccagtctga agttgcgggt gtcaaacttt accccgatgt cgcttttccag | 1140 |
| aaccccgttc tgtctgccca ctttcaagta gtgctccacg atcgcgttgt tcataaggtc | 1200 |
| tatggtcatg gtctcggagt agttgccctc gggcagcgtg aactccaccc actcgtattt | 1260 |
| cagctccacc tgattgtcct tagtaggcaa gcgcgacacc atcacccgcg ccttaaactt | 1320 |
| attggtaaac atgaactcgt tcacatttgg catgttggta tgcaggatgg ttttcaggtc | 1380 |
| gccgccccag tgcgaccggt cgtcaagatt gatggtctgt gtgcttgcct cccccgggct | 1440 |
| gtagtcattg ttttgaatga ccgtggtcag aaagttgctg tggtcgttct ggtagttcag | 1500 |

```
ggatgccaca tccgttgact tgttgtccac caggtacaca cgggtggtgt cgaataggg      1560 tgccaactca gagtaacgga tgctgtttct ccccccggta ggccgcaggt accgcggagg      1620
cacaaacggc gggtccaggg gagcatcgaa gggagaaccc agcgccgccg ccactggcgc      1680
cgcgctcacc acactctcgt aggagggagg aggaccttcc tcatacatcg ccgcgcgccg      1740
catggatcca cttccaccac ttccaccgta cagctcctcc gccttttctt ggttttggac      1800
tttcatgggc acattctcag tacatcttgc tccagtgaat ccaggttggc acttgcacaa      1860
gtatctcgag gggtttgaaa ggtctttcac catgaagcac tcccctccat tcacacagaa      1920
agttttctcc ttctccgcac attttacaag atggcttgtc ccagtggtgg atgtagatgt      1980
agatgaagaa gtatttgctc cttctgtgga tactgatatt ctaatgggag actctgaaga      2040
cacatatgct ccttcagttg aggctggcat accagtgatg atctcgtttg attccacgat      2100
ggtgatattg gcagaggcac tgtcatttcc taatttgctg atcactttgc acatatactc      2160
tccagaatca gccagtgatg ctttgttaat gcgaagttct gacttccctg gcttttttg       2220 tatcttgata ttttgtggtt tgttttttcg attcaattca ttcccattct tgaaccactt      2280
gaatctgaga gaggagtatt cagaactggt ttcacaccga aggactagtt tggaacctgc      2340
agccgattcc tggcttttca tctctttcaa tcggggaggc aa                        2382

<210> SEQ ID NO 6
<211> LENGTH: 30
<212> TYPE: DNA
<213> ORGANISM: Homo sapiens

<400> SEQUENCE: 6
cgcctgagca acgcggcggg catccgcaag                                       30

<210> SEQ ID NO 7
<211> LENGTH: 30
<212> TYPE: DNA
<213> ORGANISM: Homo sapiens

<400> SEQUENCE: 7
cttgcggatg cccgccgcgt tgctcaggcg                                       30

<210> SEQ ID NO 8
<211> LENGTH: 48
<212> TYPE: DNA
<213> ORGANISM: Homo sapiens

<400> SEQUENCE: 8
gactacagat ctcatcatca tcatcatcat gagctcaagc aggaattc                   48

<210> SEQ ID NO 9
<211> LENGTH: 48
<212> TYPE: DNA
<213> ORGANISM: Homo sapiens

<400> SEQUENCE: 9
gaattcctgc ttgagctcat gatgatgatg atgatgagat ctgtagtc                   48

<210> SEQ ID NO 10
<211> LENGTH: 571
<212> TYPE: PRT
<213> ORGANISM: Homo sapiens

<400> SEQUENCE: 10
```

-continued

```
Met Arg Arg Ala Ala Met Tyr Glu Glu Gly Pro Pro Ser Tyr Glu
1               5                   10                  15

Ser Val Val Ser Ala Ala Pro Val Ala Ala Leu Gly Ser Pro Phe
                20                  25                  30

Asp Ala Pro Leu Asp Pro Pro Phe Val Pro Pro Arg Tyr Leu Arg Pro
                35                  40                  45

Thr Gly Gly Arg Asn Ser Ile Arg Tyr Ser Glu Leu Ala Pro Leu Phe
50                  55                  60

Asp Thr Thr Arg Val Tyr Leu Val Asp Asn Lys Ser Thr Asp Val Ala
65                  70                  75                  80

Ser Leu Asn Tyr Gln Asn Asp His Ser Asn Phe Leu Thr Thr Val Ile
                85                  90                  95

Gln Asn Asn Asp Tyr Ser Pro Gly Glu Ala Ser Thr Gln Thr Ile Asn
                100                 105                 110

Leu Asp Asp Arg Ser His Trp Gly Gly Asp Leu Lys Thr Ile Leu His
                115                 120                 125

Thr Asn Met Pro Asn Val Asn Glu Phe Met Phe Thr Asn Lys Phe Lys
                130                 135                 140

Ala Arg Val Met Val Ser Arg Leu Pro Thr Lys Asp Asn Gln Val Glu
145                 150                 155                 160

Leu Lys Tyr Glu Trp Val Glu Phe Thr Leu Pro Glu Gly Asn Tyr Ser
                165                 170                 175

Glu Thr Met Thr Ile Asp Leu Met Asn Asn Ala Ile Val Glu His Tyr
                180                 185                 190

Leu Lys Val Gly Arg Gln Asn Gly Val Leu Glu Ser Asp Ile Gly Val
                195                 200                 205

Lys Phe Asp Thr Arg Asn Phe Arg Leu Gly Phe Asp Pro Val Thr Gly
                210                 215                 220

Leu Val Met Pro Gly Val Tyr Thr Asn Glu Ala Phe His Pro Asp Ile
225                 230                 235                 240

Ile Leu Leu Pro Gly Cys Gly Val Asp Phe Thr His Ser Arg Leu Ser
                245                 250                 255

Asn Leu Leu Gly Ile Arg Lys Arg Gln Pro Phe Gln Glu Gly Phe Arg
                260                 265                 270

Ile Thr Tyr Asp Asp Leu Glu Gly Gly Asn Ile Pro Ala Leu Leu Asp
                275                 280                 285

Val Asp Ala Tyr Gln Ala Ser Leu Lys Asp Asp Thr Glu Gln Gly Gly
                290                 295                 300

Gly Gly Ala Gly Gly Ser Asn Ser Ser Gly Ser Gly Ala Glu Glu Asn
305                 310                 315                 320

Ser Asn Ala Ala Ala Ala Met Gln Pro Val Glu Asp Met Asn Asp
                325                 330                 335

His Ala Ile Arg Gly Asp Thr Phe Ala Thr Arg Ala Glu Glu Lys Arg
                340                 345                 350

Ala Glu Ala Glu Ala Ala Glu Ala Ala Pro Ala Ala Gln Pro
                355                 360                 365

Glu Val Glu Lys Pro Gln Lys Lys Pro Val Ile Lys Pro Leu Thr Glu
                370                 375                 380

Asp Ser Lys Lys Arg Ser Tyr Asn Leu Ile Ser Asn Asp Ser Thr Phe
385                 390                 395                 400

Thr Gln Tyr Arg Ser Trp Tyr Leu Ala Tyr Asn Tyr Gly Asp Pro Gln
                405                 410                 415

Thr Gly Ile Arg Ser Trp Thr Leu Leu Cys Thr Pro Asp Val Thr Cys
```

```
                    420                 425                 430
Gly Ser Glu Gln Val Tyr Trp Ser Leu Pro Asp Met Met Gln Asp Pro
            435                 440                 445

Val Thr Phe Arg Ser Thr Arg Gln Ile Ser Asn Phe Pro Val Val Gly
            450                 455                 460

Ala Glu Leu Leu Pro Val His Ser Lys Ser Phe Tyr Asn Asp Gln Ala
465                 470                 475                 480

Val Tyr Ser Gln Leu Ile Arg Gln Phe Thr Ser Leu Thr His Val Phe
            485                 490                 495

Asn Arg Phe Pro Glu Asn Gln Ile Leu Ala Arg Pro Pro Ala Pro Thr
            500                 505                 510

Ile Thr Thr Val Ser Glu Asn Val Pro Ala Leu Thr Asp His Gly Thr
            515                 520                 525

Leu Pro Leu Arg Asn Ser Ile Gly Gly Val Gln Arg Val Thr Ile Thr
            530                 535                 540

Asp Ala Arg Arg Arg Thr Cys Pro Tyr Val Tyr Lys Ala Leu Gly Ile
545                 550                 555                 560

Val Ser Pro Arg Val Leu Ser Ser Arg Thr Phe
            565                 570

<210> SEQ ID NO 11
<211> LENGTH: 10
<212> TYPE: PRT
<213> ORGANISM: Homo sapiens

<400> SEQUENCE: 11

Lys Lys Lys Lys Lys Lys Lys Lys Lys Lys
1               5                   10

<210> SEQ ID NO 12
<211> LENGTH: 33
<212> TYPE: DNA
<213> ORGANISM: Homo sapiens

<400> SEQUENCE: 12
atcgaaggat ccatgcggcg cgcggcgatg tat                              33
```

SELF-ASSEMBLING COMPLEX FOR TARGETING CHEMICAL AGENTS TO CELLS

RELATED APPLICATIONS

The present application is a divisional of U.S. Ser. No. 12/667,436, filed on Dec. 31, 2009, which in turn is an application filed under 35 U.S.C. §371 based on the International Application PCT/US2008/069239 filed on Jul. 3, 2008, which in turn claims priority to the U.S. Provisional Application Ser. No. 60/948,242, filed on Jul. 6, 2007, all of which applications are incorporated by reference herein in their entirety, including the drawings.

STATEMENT REGARDING FEDERALLY SPONSORED RESEARCH OR DEVELOPMENT

This invention was made with government support under Grant No. CA129822, Grant No. CA102126, and Grant No. CA116014 awarded by National Institutes of Health. The government has certain rights in the invention.

SEQUENCE LISTING

The instant application contains a Sequence Listing which has been submitted in ASCII format via EFS-Web and is hereby incorporated by reference in its entirety.

FIELD OF THE INVENTION

The invention relates to the field of biotechnology; specifically, to delivery systems for chemical agents.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Current strategies for targeting therapy to tumors include antibody-targeted chemotherapy agents (i.e., immunoconjugates), targeted toxins, signal-blocking antibodies, and antibody-targeted liposomes (i.e., immunoliposomes). In fact, HER2+ breast tumors, which over-express subunit 2 of the human epidermal growth factor receptor (HER), comprise a significant subset of breast cancers that are recalcitrant to standard methods of treatment, and predict a high mortality. The abnormally high level of HER on the surface of these tumor cells may enable targeted therapeutics to home in on these cells, thus making HER2+ tumors ideal candidates for targeted therapy. However, the aforementioned therapies are problematic—with respect to HER2+ breast tumors and other forms of cancer—because they require chemical modification which may be costly and can impair activity of the drug and/or the carrier; may use recombinant antibodies that can lose structure in physiological conditions and thus result in impaired targeting activity; are not able to penetrate into the cell; focus on the need to modulate receptor signaling which can be impaired in tumor cells; and have off-target effects such as heart toxicity.

Immunoconjugate therapies rely on the chemical coupling of single-chain antibodies to drugs, whereby the antibody directs the drug to specific cells by recognizing certain cell surface proteins or receptors [K. A. Chester et al., *Disease Markers*, 16:53-62 (2000); A. E. Frankel et al., *Clin. Cancer Res.*, 6:326-334 (2000)]. Studies have shown, however, that such antibodies can unfold and aggregate at physiological temperature, which would impede binding to target cells, and result in low therapeutic efficacy [R. Glockshuber et al., *Biochem*, 29:1362-1367 (1990); M. Schmidt et al., *Oncogene*, 18:1711-1721 (1999)]. Moreover, covalent linkage of drug to carrier can impair the activity of both molecules, as well as entail high production cost.

In contrast, studies in connection with one embodiment of the present invention show that an exemplary targeted carrier protein, HerPBK10, retains receptor targeting under physiological conditions in the presence of serum, indicating that the targeted carrier does not unfold or lose receptor binding [H. Agadjanian et al., *Pharm Res.*, 23:367-377 (2006)]. Furthermore, the present invention is engineered so that the drug self-assembles with the carrier molecule and thus does not require chemical modifications to covalently link the molecules together. This non-covalent assembly thus allows both the targeted carrier and drug to remain unmodified and thus preserve structure and activity. Finally, recombinant proteins (such as HerPBK10) can be produced in bulk quantities by large-scale fermentation for a lower cost compared to monoclonal antibody generation and production.

An alternative approach to tumor targeting has been the development of toxic proteins, such as plant or bacterial toxins, that are modified by appendage to a targeting peptide (or ligand) [A. E. Frankel et al., *Clin. Cancer Res.*, 6:326-334 (2000)]. Such proteins are produced by recombinant methods (i.e., genes are engineered to produce the proteins in a cell system, from which the proteins can then be isolated), and the resulting protein is a fusion of the toxin to the ligand. While fusion toxin proteins can be produced by large scale fermentation as a more efficient and lower cost alternative to antibody generation, the toxin requires special processing to be active, thus limiting potency [M. Schmidt et al., *Oncogene*, 18:1711-1721 (1999); M. Jeschke et al., *Intl. J. Cancer*, 60:730-739 (1995)]. For example, the activity of recombinant diptheria toxin transmembrane domain, used to enhance non-viral gene transfer, is reduced by as much as 75% when fused to a foreign peptide, indicating that appending a peptide to a toxin disables toxin activity [K. J. Fisher and J. M. Wilson, *Biochem. J.*, 321:49-58 (1997)]. Thus, delivery by non-covalent means (i.e., self-assembly), which is a feature of the present invention, is believed to be advantageous in terms of retaining drug potency.

Antibodies directed at the extracellular domain of HER2 have been used to target drug complexes to the HER2 subunit, but have not necessarily induced internalization of the drug complex; thus limiting potency [D. Goren et al., *Br. J. Cancer*, 74:1749-1756 (1996)]. Such findings illustrate that targeting is not enough, as a lack of targeted uptake can limit efficacy. Alternatively, signal blocking antibodies have been developed to inhibit the proliferative signal transduced through overexpression and high cell surface display of HER2 [J. Baselga et al., *J. Clin. Oncol.*, 14:737-744 (1996); M. A. Cobleigh et al., *Proc. Am. Soc. Clin. Oncol.*, 17:97a (1998)]. One currently used targeted therapy, trastuzumab (Herceptin), an antibody directed against the HER2 subunit, blocks normal signaling but has been ineffective in about 70% of treated patients, possibly due to aberrant intracellular pathways in tumor cells that may not respond to signal inhibition [C. L. Vogel et al., "*J. Clin. Oncol.*, 20:719-726 (2002); T. Kute et al., *Cytometry*, A57:86-93 (2004)]. Furthermore, an ongoing concern with trastuzumab is the exquisite sensitivity of heart tissue to HER2 signal inhibition, which is further exacerbated by anthracycline chemotherapy agents [D. J. Slamon et al., *N. Engl. J. Med.*, 344:783-792 (2001)]. In one embodiment, the approach of the present invention instead takes advantage of the binding interaction of the natural ligand for HER, which has a greatly increased ligand affinity when HER2 is overexpressed. It is believed that this is likely to translate to lower, and thus safer, doses of drug when targeted. Accordingly, the targeting approach of the present invention should avoid binding to tissues displaying low to normal receptor subunit levels but exhibit preferential binding to HER2+ tumor cells. Moreover, the inventor has shown that the receptor binding domain of heregulin that is incorporated into HerPBK10 induces rapid internalization after binding to the heregulin receptor [L. K. Medina-Kauwe et al., *BioTechniques*, 29:602-609 (2000); L. K. Medina-Kauwe and X. Chen, Vitamins and Hormones, Elsevier Science, G. Litwack (Ed.), San Diego, 81-95 (2002)]; enabling uptake of DNA [L. K. Medina-Kauwe et al., *Gene Ther.*, 8:1753-1761 (2001)] and fluorescent compounds [H. Agadjanian et al., *Pharm Res.*, 23:367-377 (2006)]. The inventive approach, therefore, circumvents the need to modulate receptor signaling, by exploiting the rapid receptor endocytosis induced by ligand binding and the cytosolic penetration features of viral capsid protein to directly transport drugs into the cell and induce cytotoxicity from within.

While targeted uptake facilitates drug entry into target cells, the intracellular disposition of the drug can still affect potency. Targeting antibodies delivering covalently linked drugs can be trafficked to lysosomes, thus sequestering the drug from subcellular targets and limiting potency. Approaches to circumventing this include linking the drug to a targeting antibody via an acid labile bond to facilitate release into the endocytic compartment [P. A. Trail et al., *Cancer Immunol Immunother.*, 52:328-337 (2003); P. A. Trail et al., *Cancer Res.*, 52:5693-5700 (1992); P. A. Trail et al., *Science*, 261:212-215 (1993); G. R. Braslawsky et al., *Cancer Res.*, 50:6608-6614 (1990)]. However, bond instability can reduce in vivo potency, likely by causing premature drug release and thus delivery to non-target tissue. In contrast, the endosomal disruption feature of one embodiment of the present invention has the advantage of endosomal escape, thus facilitating release of the drug into the cell cytoplasm and access to intracellular targets, which can include passengering of nuclear targeted molecules and passage through nuclear pores.

Immunoliposomes, carrying doxorubicin ("Dox") and targeted to HER2, have been developed and can accumulate in tumor tissue in animal models [J. W. Park et al., *Clin. Cancer Res.*, 8:1172-1181 (2002)], likely due to the leaky tumor vasculature D. C. Drummond et al., *Pharmacol. Rev.*, 51:691-743 (1999)]. Release of Dox from these liposomes is thought to occur via the acidic tumor environment, lipase release from dying cells, and enzyme and oxidizing agent release from infiltrating inflammatory cells [G. Minotti et al., *Pharmacol. Rev.*, 56:185-229 (2004)]. These conditions may induce premature drug release and nonspecific delivery, though the accumulation of immunoliposomes at tumor sites may tend to favor drug uptake at the tumor. Studies using the trastuzumab Fab' fragment for liposome targeting of Dox have demonstrated antitumor efficacy [J. W. Park et al., *Clin. Cancer Res.*, 8:1172-1181 (2002], though the effect on cardiac tissue was not reported in that study. In contrast, for reasons described above, it is believed that in an embodiment, the inventive system yields effective targeted drug delivery due to high affinity receptor-ligand binding and rapid endocytosis coupled with the membrane-penetrating activity of the viral penton base protein to ensure delivery into target cells.

SUMMARY OF THE INVENTION

Various embodiments provide a drug delivery molecule, comprising a polypeptide sequence adapted to target and/or penetrate a type of cell, a nucleic acid sequence bound to the polypeptide sequence via electrostatic interactions, and a chemical agent non-covalently linked to the nucleic acid sequence. In other embodiments, the polypeptide sequence comprises a targeting ligand, an endosomolytic domain, a positively charged domain, and/or a polylysine motif. In other embodiments, the chemical agent is doxorubicin, or a pharmaceutically equivalent thereof. In other embodiments, the type of cell is a HER2+ breast cancer cell.

Other embodiments provide a self-assembling complex, comprising a recombinant fusion protein, and a double-stranded oligonucleotide, bound to the recombinant fusion protein by electrostatic interactions. In another embodiment, the recombinant fusion protein comprises a Her segment. In another embodiment, the recombinant fusion protein comprises a penton base segment. Various embodiments also include a decalysine segment.

Other embodiments also include a method of preparing a drug delivery molecule, comprising the following steps of incubating an intercalating drug with a polynucleotide sequence to create a complex, and incubating said complex with a targeted carrier protein to form the drug delivery molecule. In another embodiment, the intercalating drug is doxorubicin, or a pharmaceutically equivalent thereof. Various other embodiments provide for the polynucleotide sequence to be double-stranded. In other embodiments, the targeted carrier protein comprises a targeting ligand. In another embodiment, the targeting ligand comprises the receptor binding domain of heregulin-α. In another embodiment, the targeted carrier protein contains an endosomolytic domain. In another embodiment, the endosomolytic domain comprises an Arg-Gly-Asp motif. In another embodiment, the endosomolytic domain comprises a Glu-Gly-Asp motif. In other embodiments, the targeted carrier protein comprises a polylysine motif. In other embodiments, the polylysine motif is a decalysine. In other embodiments, the polynucleotide sequence is SEQ. ID. NO.: 6, SEQ. ID. NO.: 7, SEQ. ID. NO.: 8, SEQ. ID. NO.: 9, or a combination thereof.

Various embodiments provide methods of treating a disease in an individual, comprising providing a drug delivery molecule comprising a polypeptide sequence adapted to target and/or penetrate a type of cell, a nucleic acid sequence bound to the polypeptide sequence via electrostatic interactions, a chemical agent non-covalently linked to the nucleic acid sequence, and administering a therapeutically effective amount of the drug delivery molecule to the individual to treat the disease. In another embodiment, the disease is breast cancer. In other embodiments, the chemical agent is a chemotherapeutic agent. In other embodiments, the chemical agent is doxorubicin, or a pharmaceutically equivalent thereof. In other embodiments, the targeted carrier protein comprises a targeting ligand, an endosomolytic domain, and/or a polylysine motif. In other embodiments, the individual is a human. In other embodiments, the individual is a mouse. In other embodiments, the type of cell is a glioma cell. In other embodiments, the polypeptide sequence is PBK10. In other embodiments, the disease is metastatic cancer.

Other embodiments include a composition comprising a drug delivery molecule comprising a polypeptide sequence adapted to target and/or penetrate a type of cell, a nucleic acid sequence bound to the polypeptide sequence via electrostatic interactions, and a chemical agent non-covalently linked to the nucleic acid sequence, and a carrier. In another embodiment, the polypeptide sequence comprises an endosomolytic domain.

Other features and advantages of the invention will become apparent from the following detailed description, taken in conjunction with the accompanying drawings, which illustrate, by way of example, various embodiments of the invention.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 4 (A) illustrates relative Dox in filtrates. After the first Dox removal spin (Wash 1) the filters were washed 4 more times with HEPES buffered saline (HBS) (Washes 2-5). FIG. 4 (B) illustrates UV/V absorbances of filtrates and retentates.

As illustrated in FIG. 6 (A), HerDox was incubated up to 12 days at 4° C., RT, or 37° C. Samples were filtered through ultrafiltration spin columns every other day, and retentate and filtrate absorbances measured at 480 nm to determine relative Dox retention or release from conjugates, respectively. As illustrated in FIG. 6 (B), to mimic extended exposure to cells in culture medium, HerDox immobilized on Ni-NTA beads were incubated with bovine serum in DMEM for the indicated times at 37° C. before each sample was pelleted. Absorbance of supernatants (Filtrates) and bead eluates (Retentates) were measured at 480 nm to detect Dox. Relative Dox release or retention in serum is expressed as normalized to control (corresponding sample lacking serum). N=3 per time point. T tests (P≤0.05) of samples compared to controls showed no significant differences.

FIG. 7 upper panel illustrates the effect of HerDox on MDA-MB-231 (HER2−) and MDA-MB-435 (HER2+) cell survival. Relative surviving cell numbers are represented as a % of corresponding untreated cells. FIG. 7 lower panel illustrates comparison of HerDox, Dox alone, or HerPBK10 alone on HER2− and HER2+ cell survival. Relative survival (as % of untreated cells) is shown for Day 3 of treatment.

As illustrated in FIG. 9 (B), cell survival was determined by calculating the relative doubling time (DT) of experimental (exp) cells normalized by control (con) cells based on the crystal violet stains (total cells) and GFP fluorescence (MDA-MB-231 cells). The DT of MDA-MB-435 was determined by subtracting the DT of MDA-MB-231 from the total cell DT. Relative survival is shown for Day 2 of treatment. As illustrated in FIG. 9 (C), there is stability in cell culture. Aliquots of culture media containing HerDox (after incubation for the indicated times at 37° C.) were electrophoresed on a 2% agarose gel. HerDox incubated at 37° C. in HEPES-buffered saline, lacking serum, was processed in parallel. Dox fluorescence was visualized by UV excitation. Free Dox (Dox alone) is not retained in the gel whereas Dox incorporated in HerDox is. To align fluorescent bands with HerPBK10 and assess loading per lane, the gel was stained with Coomassie blue, which also identified serum protein from culture media samples.

FIG. 10 illustrates preferential targeting of GFP-Her to HER2+ tumors. Tumor-bearing mice were injected with 3 nmoles of GFP-Her via the tail vein. Tissues were harvested at 3.5 h after injection and visualized using a Xenogen small-animal imager. GFP fluorescence is pseudo-colored red (blue pseudo-coloring indicates no fluorescence whereas GFP intensity is reflected by a color value shift toward red in the color bar).

FIG. 11 (A) depicts imaging of live mice after IV delivery of HerDox. Tumors are indicated by arrows. FIG. 11 (B) depicts imaging of tumors and tissues harvested at 3 h after injection of HerDox or Dox. Fluorescence signal from Dox is pseudo-colored according to the color bar, with a shift toward 100 indicating high fluorescence intensity. FIG. 11 (B) illustrates a comparison of the targeted delivery of Dox to HER2+ breast cancer cells with minimal delivery to other organs and tissues using a delivery system in accordance with an embodiment of the present invention (left panel), as compared with Dox administered alone (right panel).

FIG. 17 (A) depicts a graph of relative cell surface HER subunit levels as measured by ELISA. Cells were incubated with anti-HER subunit antibodies followed by HRP-conjugated secondary antibodies using standard procedures. Relative cell numbers were measured by crystal violet staining and quantified by measuring crystal violet absorbance at 590 nm. Relative subunit levels are reported as the ELISA signal of each cell population normalized by the relative cell number, or Abs 450 nm/590 nm. FIG. 17 (B) depicts toxicity to cells displaying differential HER2. Cytotoxicities from a range of HerDox doses were assessed on each cell line by metabolic assay and confirmed by crystal violet stain. CD50 values shown in log scale were determined by non-linear regression analyses of HerDox dose curves using a scientific graphing program and confirmed using a calculator. The relative HER2 level of each cell line is shown next to each CD50 value.

FIG. 20 (A) depicts HER immunofluorescence on U251 human glioma cells. Images were captured using laser scanning fluorescence confocal microscopy. FIG. 20 (B) depicts a graph of HerDox vs. Dox toxicity to U251 cells. Significant differences were determined by 2-tailed tests.

DETAILED DESCRIPTION

Figure 1:
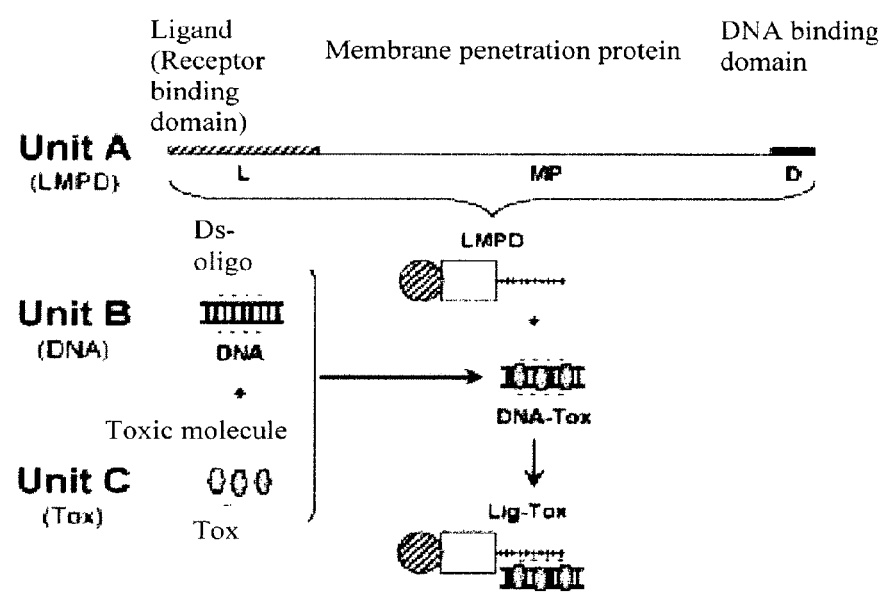
FIG. 1 illustrates a delivery system in accordance with an embodiment of the present invention.

The invention is based on a novel delivery system including a self-assembling complex for targeting chemical agents to cells. It is believed to be advantageous because, among other things, it is self-assembling and less expensive to produce relative to conventional systems via large scale fermentation. It is capable of targeting diseased cells in vitro and in vivo, avoids heart tissue (where desirable to do so), and binds and penetrates into target cells. Furthermore, the complex is assembled non-covalently (i.e., without the need for chemical coupling of, for instance, a chemotherapeutic to a targeted carrier) and it uses a small nucleic acid carrier as a bridge to assemble the drug with the targeted protein carrier vehicle.

As will be readily appreciated by those of skill in the art, the invention may have application in a wide variety of fields, including various fields of medicine and the diagnosis, prognosis and treatment of disease. In one embodiment, the invention provides a mechanism for the treatment of cancer by enabling the targeted delivery of chemotherapeutic agents to cancer cells. In other embodiments, the inventive system may be used to target other types of cells and thereby deliver other chemical agents as may be desired. In another embodiment, the invention provides a mechanism for the imaging of particular cells or tissues, by the targeted delivery of imaging agents to such tissues or cells (e.g., cancer cells). Suitable imaging agents will be readily recognized by those of skill in the art, and may be used in connection with, for example, magnetic resonance imaging of cancer cells with contrast agents.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001); and Sambrook and Russel, Molecular Cloning: A Laboratory Manual 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, preventing, reducing, preventing the increase of and inhibiting the proliferation or growth of cancer cells or tumors. Beneficial results may also refer to curing the cancer and prolonging a patient's life or life expectancy.

"Cancer" and "cancerous" refer to or describe the physiological condition in mammals that is typically characterized by unregulated cell growth. Examples of cancer include, but are not limited to, ovarian cancer, breast cancer, colon cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, head and neck cancer, and brain cancer.

"Curing" cancer includes degrading a tumor such that a tumor cannot be detected after treatment. The tumor may be reduced in size or become undetectable, for example, by atrophying from lack of blood supply or by being attacked or degraded by one or more components administered according to the invention.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Prevention" as used herein refers to efforts undertaken to hinder the development or onset of a condition or cancer condition even if the effort is ultimately unsuccessful.

"Condition" as used herein refers to an illness or physical ailment.

"Therapeutically effective amount" as used herein refers to that amount which is capable of achieving beneficial results in a patient with cancer. A therapeutically effective amount can be determined on an individual basis and will be based, at least in part, on consideration of the physiological characteristics of the mammal, the type of delivery system or therapeutic technique used and the time of administration relative to the progression of the disease.

"Treatment" and "treating," as used herein refer to both therapeutic treatment and prophylactic or preventative measures, wherein the object is to achieve beneficial results even if the treatment is ultimately unsuccessful.

"Tumor," as used herein refers to all neoplastic cell growth and proliferation, whether malignant or benign, and all pre-cancerous and cancerous cells and tissues.

"Chemotherapeutic agent" as used herein refers to agents with the capability to destroy, kill, hinder the growth of, and/or otherwise have a deleterious effect on cancer cells or tumors. These may include, but are in no way limited to, alkylating agents (e.g., busulfan, cisplatin, carboplatin, chlorambucil, cyclophosphamide, ifosfamide, dacarbazine, mechlorethamine, melphalan, and temozolomide), nitrosoureas (e.g., streptozocin, carmustine, and lomustine), anthracyclines and related drugs (e.g., doxorubicin, epirubicin, idarubicin, and mitoxantrone), topoisomerase I and II inhibitors (e.g., topotecan, irinotecan, etoposide and teniposide), and mitotic inhibitors (e.g., taxanes such as paclitaxel and docetaxel, and vinca alkaloids such as vinblastine, vincristine, and vinorelbine). Other chemotherapeutic agents will be understood by those of skill in the art and can be used in connection with alternate embodiments of the present invention by exercise of routine effort.

As used herein, "intercalating" refers to the ability to insert into an existing structure, such as a polynucleotide sequence.

As used herein, "Her" refers to a segment obtained from the receptor binding domain of heregulin-α, which binds to HER2/HER3 or HER2/HER4 subunit heterodimers. As used herein, "PB" refers to a penton base segment that normally mediates cell binding, entry, and cytosolic penetration of adenovirus serotype 5 during the early stages of infection. An example of a penton base protein is provided herein as SEQ. ID. NO.: 10. This penton base protein normally has an RGD motif (Arg-Gly-Asp). As used herein, "K10" refers to a decalysine motif that has the capacity to bind nucleic acids by electrophilic interaction, provided herein as SEQ. ID. NO.: 11. An example of a nucleotide sequence coding for HerPBK10 is provided herein as SEQ. ID. NO.: 4 with its complement strand of SEQ. ID. NO.: 5. Similarly, a point mutation of the RGD motif may be used to create an EGD motif (Glu-Gly-Asp), resulting in a HerPBrgdK10 polypeptide molecule (rather than HerPBK10).

As readily apparent to one of skill in the art, any number of polynucleotide sequences or small double-stranded nucleic acids may be used in accordance with various embodiments described herein. For example, in one embodiment, SEQ. ID. NO.: 6, SEQ. ID. NO.: 7, SEQ. ID. NO.: 8, SEQ. ID. NO.: 9, or a combination thereof, may be used as a polynucleotide sequence or double stranded nucleic acid.

As known to one of skill in the art, any number of targeting ligands may be used in accordance with various embodiments described herein. For example, PB itself may act as a targeting ligand of PBK10 when targeting integrins such as $α_vβ_3$. As known by one of skill in the art, integrins are overly expressed in various types of metastatic tumors. Thus, in conjunction with various embodiments described herein, PBK10 may be used to target metastatic tumors and cells with a high expression of integrins.

The inventive delivery system includes a complex that can be administered to a mammal by various routes of administration, whereupon it hones in on target cells (e.g., cancer cells) to deliver molecules such as imaging agents or therapeutic agents into the cells. In one embodiment, the complex provides for delivery of therapeutic agents to cancer cells while sparing normal, healthy cells. Current methods of targeted delivery therapy fail due to the many off-target effects of the therapy and use of chemical modification strategies that impair therapeutic activity. One advantage of the inventive delivery system is its targeting effects and retention of delivered agents' therapeutic activity.

As shown in FIG. 1, an embodiment of the inventive delivery system includes three components that self-assemble into one targeted conjugate. The first component ("Unit A") is a unique cell-penetrating protein that can target and penetrate a particular type of cell(s). It includes a ligand (receptor binding domain), a membrane penetration domain, and a DNA binding domain. The second component ("Unit B") is a small nucleic acid (e.g., a double-stranded oligonucleotide) that binds to Unit A via electrostatic interactions. The third component ("Unit C") is a chemical agent that can bind Unit B via intercalation interactions. In one embodiment of the present invention, the type of cell is a cancer cell, and the chemical agent is a chemotherapeutic agent. In another embodiment of the present invention, the type of cell is HER2+ breast cancer cells, and the chemical agent is Dox, or a pharmaceutically equivalent thereof.

In various embodiments, the inventive delivery system can be incorporated into a pharmaceutical composition, which may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or in the form of lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulating, and compressing, when necessary, for tablet forms; or milling, mixing and filling for producing hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to, the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Typical dosages of the inventive delivery system and, more specifically, the therapeutic agents (e.g., chemotherapeutic agents), particularly Dox, and/or the imaging agents delivered by it can be in the ranges recommended by the manufacturer where known therapeutic compounds or imaging agents are used, and also as indicated to the skilled artisan by the in vitro responses or responses in animal models. The actual dosage will depend upon the judgment of the physician, the condition of the patient, and the effectiveness of the therapeutic method.

The invention also relates to methods of treating diseases by administration to a mammal in need thereof of a therapeutically effective amount of the delivery system of the invention including a therapeutic agent appropriate to treat the disease. In one embodiment of the invention, the disease is cancer and the therapeutic agent is a chemotherapeutic agent. In another embodiment of the invention, the disease is breast cancer and/or HER2+ breast cancer, and the therapeutic agent is Dox.

The invention also relates to methods of diagnosing and/or prognosing a disease in a mammal by administering to the mammal an effective amount of the delivery system of the invention including an imaging agent appropriate to enable the imaging of cells and/or tissues relevant to the disease. In one embodiment of the invention, the disease is cancer and an imaging agent is delivered to image cancerous cells or tissue. In another embodiment of the invention, the disease is breast cancer and/or HER2+ breast cancer. The methods may include administration of the delivery system with a suitable imaging agent and the use of conventional imaging techniques to thereafter image the target tissue or cells and thereby diagnose and/or prognose the disease condition.

In still further embodiments of the present invention, the aforementioned methods may be used in concert to, for example, image cells or tissues relevant to a disease and then treat the disease. For instance, in one embodiment of the present invention, an imaging agent may be delivered with the inventive delivery system; enabling the diagnosis of HER2+ breast cancer. The inventive delivery system may then be utilized to deliver a chemotherapeutic agent (e.g., Dox, or pharmaceutically equivalent thereof) to the HER2+ breast cancer cells.

The present invention is also directed to a kit to treat cancer, including, but in no way limited to, breast cancer and more particularly HER2+ breast cancer. The kit is useful for practicing the inventive method of treating such conditions. The kit is an assemblage of materials or components, including at least one of the components of the inventive delivery system. Thus, in some embodiments, the kit contains the various components of the inventive delivery system. In other embodiments, the kit contains all components of the inventive delivery system with the exception of the chemotherapeutic agent to be delivered therewith.

The exact nature of the components configured in the inventive kit depends on its intended purpose. For example, some embodiments are configured for the purpose of treating the aforementioned conditions in a subject in need of such treatment. The kit may be configured particularly for the purpose of treating mammalian subjects. In another embodiment, the kit is configured particularly for the purpose of treating human subjects. In further embodiments, the kit is configured for veterinary applications, for use in treating subjects such as, but not limited to, farm animals, domestic animals, and laboratory animals.

Other embodiments are configured for the purpose of imaging particular cells or tissues in a subject in whom the imaging of such cells or tissues is desirable. The kit may be configured particularly for the purpose of imaging cells or tissues in mammalian subjects. In another embodiment, the kit is configured particularly for the purpose of imaging cells or tissues in human subjects, including, but in no way limited to, breast cancer cells and more particularly HER2+ breast cancer cells. In further embodiments, the kit is configured for veterinary applications, for use in imaging cells and tissues in subjects such as, but not limited to, farm animals, domestic animals, and laboratory animals. In other embodiments, the kit contains all components of the inventive delivery system with the exception of the imaging agent to be delivered therewith.

Instructions for use may be included in the kit. "Instructions for use" typically include a tangible expression describing the technique to be employed in using the components of the kit to effect a desired outcome, such as to treat a disease condition (e.g., cancer) or to image particular cells or tissues in a subject. Optionally, the kit also contains other useful components such as diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in treatment of pituitary disorders and/or tumors and/or cancer. As used herein, the term "package" refers to a suitable solid matrix or material such as glass, plastic, paper, foil, and the like, capable of holding the individual kit components. Thus, for example, a package can be one or more glass vials used to contain suitable quantities of the components of the inventive delivery system in an unassembled, a partially assembled, or a completely assembled form. The packaging material generally has an external label which indicates the contents and/or purpose of the kit and/or its components.

EXAMPLES

The following example is provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Targeted Delivery of Chemotherapeutic to HER2+ Breast Cancer Cells

Figure 2:
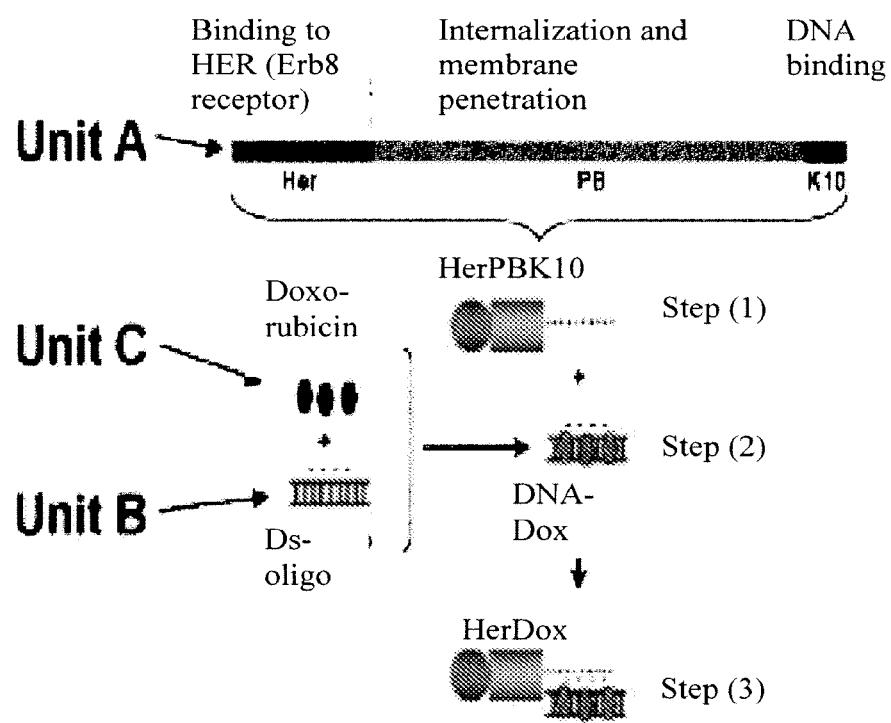
FIG. 2 illustrates a delivery system configured for the delivery of Dox to HER2+ breast cancer cells in accordance with an embodiment of the present invention. Step (1) illustrates HERPBK10 produced and purified as a recombinant fusion protein in bacterial. Step (2) illustrates DNA-Dox formed by noncovalent intercalation interaction. Step (3) illustrates DNA-Dox can bind HerPBK10 by noncovalent charge interaction (anionic DNA phosphates electrophillicaly bind cationic polylysine).

The inventive technology was tested on HER2+ breast cancer cells in vitro and in vivo. As illustrated in FIG. 2, to engineer the invention to target HER2+ breast cancer, Unit A includes a protein called HerPBK10, which can be generated by the methods described in L. K. Medina-Kauwe et al., *Gene Ther.*, 8:1753-1761 (2001), incorporated by reference herein in its entirety. HerPBK10 contains the receptor binding domain of heregulin fused to the cell penetrating adenovirus penton base protein modified by a carboxy (C)-terminal decalysine. The 'Her' segment of HerPBK10 is obtained from the receptor binding domain of heregulin-α, which binds specifically to HER2/HER3 or HER2/HER4 subunit heterodimers. Although heregulin interacts directly with HER3 or HER4, but not HER2, ligand affinity is greatly enhanced by HER2. Thus, tumor cells that over-express HER2 (i.e., HER2+ tumor cells) are believed to be good candidates for heregulin-directed targeting.

The membrane penetrating activity of the adenovirus serotype 5 (Ad5) penton base protein is incorporated into the 'PB' segment of HerPBK10 to facilitate penetration into target cells. The 'K10' segment includes ten lysine residues, whose positive charge can facilitate the transport of negatively charged molecules, such as nucleic acids, by electrophilic interaction.

Unit B includes two complementary oligonucleotides annealed together to form a small double-stranded nucleic acid. Unit C is comprised of the chemotherapy agent, Dox.

The three components are assembled together in two steps by incubation at room temperature. In step 1, the Unit B DNA is incubated with the Unit C Dox to form a DNA-Dox assembly (i.e., Unit B+Unit C). This forms by intercalation of the Dox molecules in between the DNA base pairs. In step 2, the DNA-Dox assembly is incubated with HerPBK10 to form a final complex called HerDox (i.e., Unit A+Unit B+Unit C). This interaction is formed by the electrophilic binding of the negatively charged DNA phosphate backbone to the positively charged polylysine tail of HerPBK10.

Figure 3:
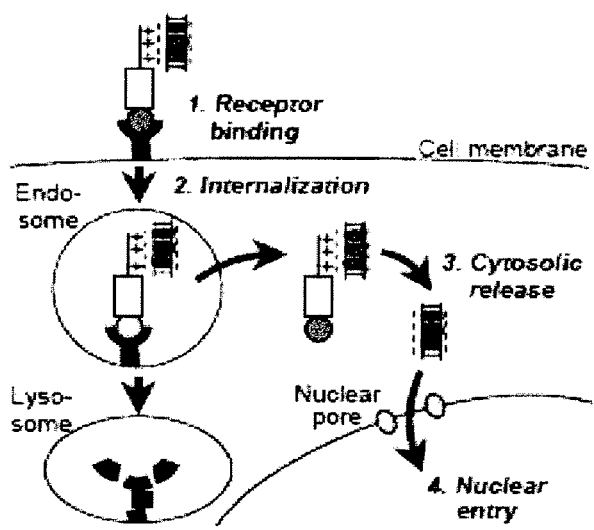
FIG. 3 illustrates a schematic of the operation of a delivery system configured for the delivery of Dox to HER2+ breast cancer cells in accordance with an embodiment of the present invention, including (1) receptor binding at the cell membrane, (2) internalization of the complex, (3) cytosolic release of the chemotherapeutic (Dox) non-covalently bonded to dsDNA via intercalation interactions, and (4) nuclear entry of the chemotherapeutic and dsDNA.
Figure 11:
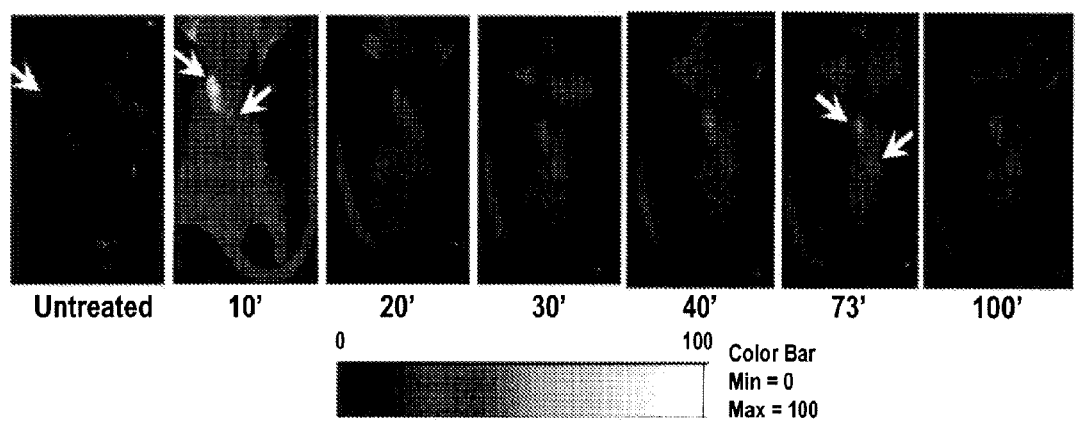
FIG. 11 (A)-(B) illustrates preferential targeting of Her-Dox to HER2+ tumors. Tumor-bearing mice were injected with 0.75 nmoles of HerDox or Dox via the tail vein and imaged with a custom small animal imager.
Figure 11:
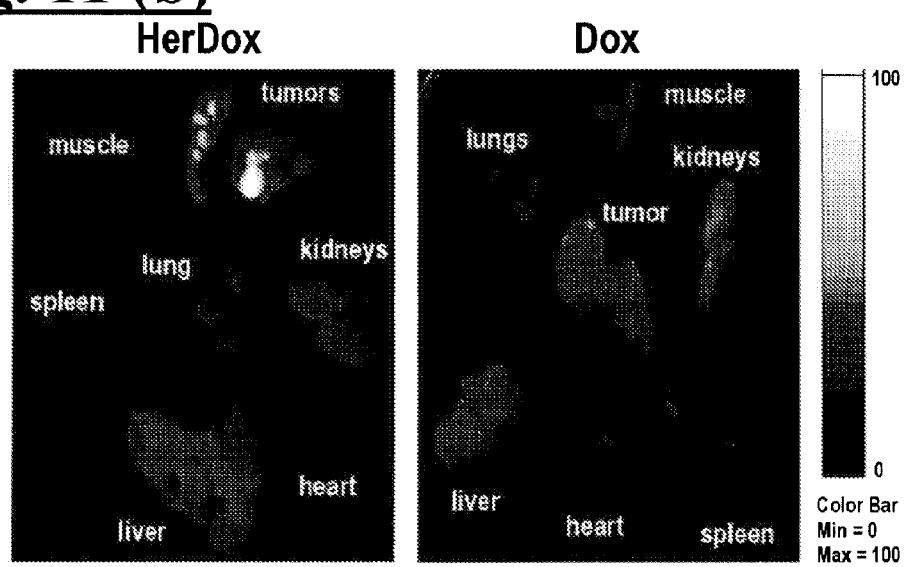

FIG. 3 illustrates a schematic of the operation of the inventive delivery system in this particular embodiment thereof, and FIG. 11 (B) illustrates its successful application, in vivo, as compared with conventional administration of Dox. Through use of the inventive delivery system, delivery of Dox was targeted to cancerous cells; relatively higher quantities of the drug were delivered to the cancerous cells as compared with conventionally delivered Dox, and relatively lower quantities of the drug reached non-target healthy tissues.

Example 2

HerDox is Highly Stable During Assembly

Figure 4:
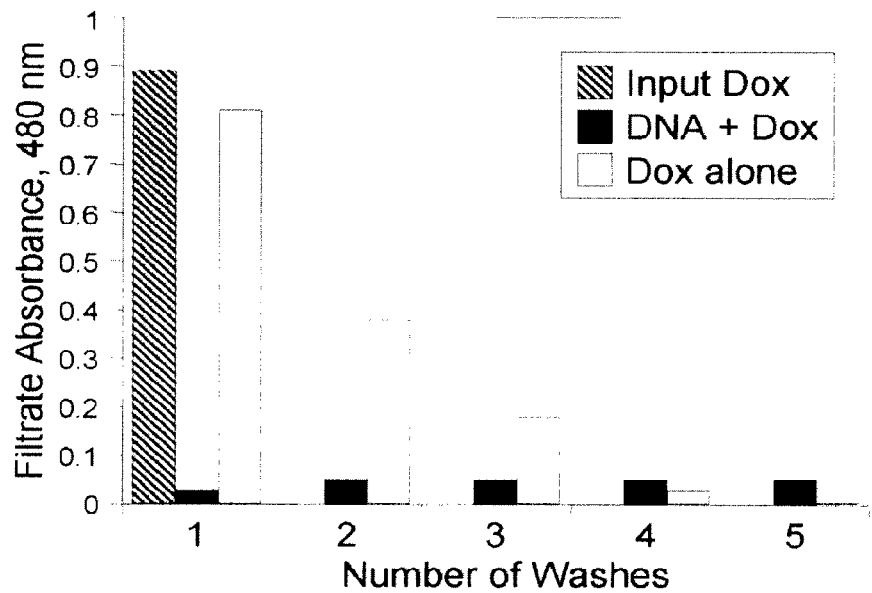
FIG. 4 (A)-(B) illustrates DNA-Dox assembly. The ds-oligo (prepared by annealing complimentary 30 bp oligonucleotides) was incubated 1 h at room temp with Dox at 1:16 molar ratio DNA:Dox. Free Dox was removed by filtration through 10 MW cutoff spin columns.
Figure 4:
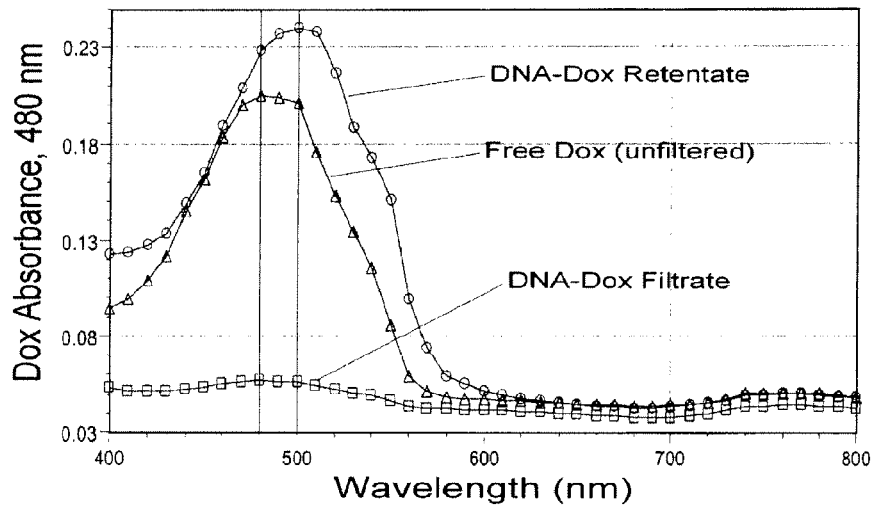
Figure 5:
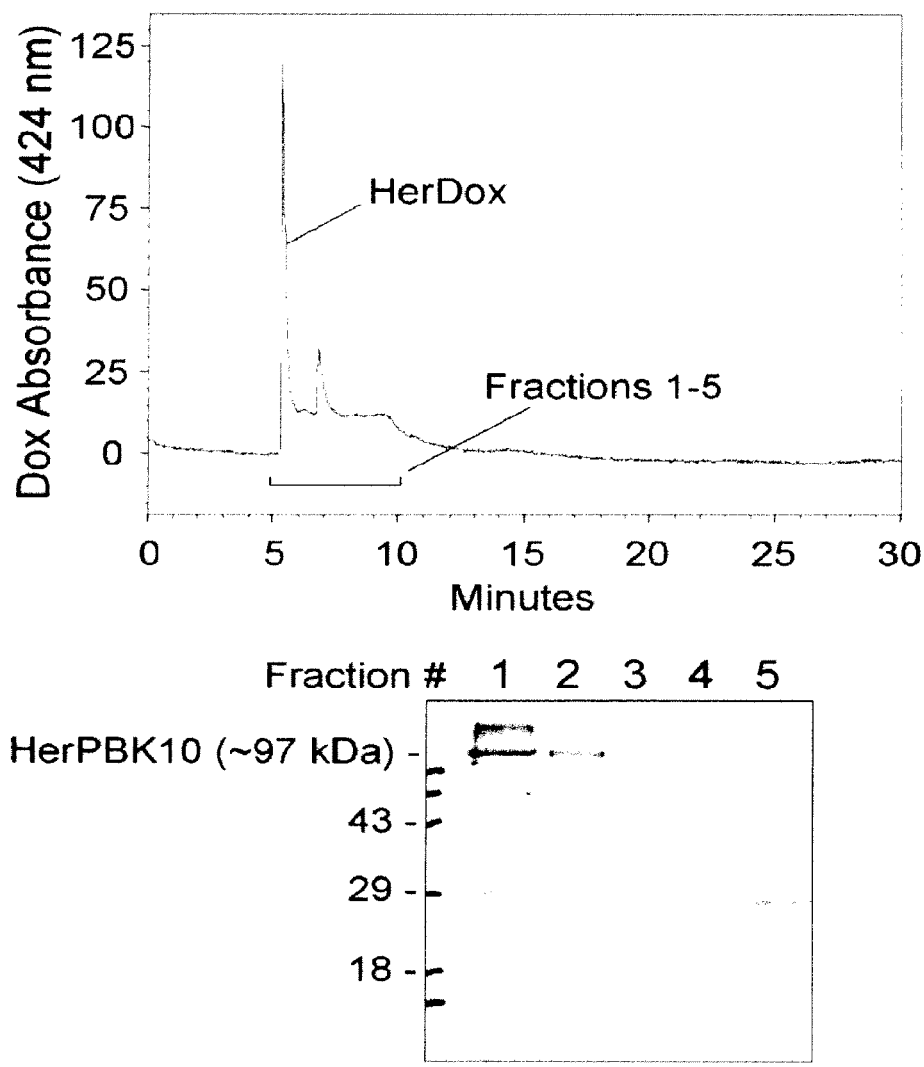
FIG. 5 illustrates HerDox assembly. DNA-Dox was incubated with HerPBK10 on ice for 2 h at 9:1 molar ratio HerPBK10:DNA-Dox. The mixture was subject to size exclusion HPLC and fractions collected at minutes 6-10 for SDS-PAGE and immunoblotting. In future experiments, HerDox is collected from the 6 min peak. The concentration of Dox in HerDox was assessed by measuring absorbance at 480 nm (Dox absorbance wavelength). HPLC purification of HerDox fractions 1-5 correspond to samples collected at minutes 6-10. Immunoblot of fractions 1-5 is also depicted with a penton base antibody used to identify HerPBK10.

HerDox consists of three components: Dox; a small double-stranded nucleic acid (which is directly responsible for carrying Dox); and the targeted protein, HerPBK10. HerDox is assembled in two steps. First, Dox is mixed with the DNA to form a DNA-Dox pair by DNA intercalation. Then, the DNA-Dox pair is mixed with HerPBK10 to form HerDox by electrophilic interaction. To separate DNA-Dox from free Dox, the mixture underwent ultrafiltration centrifugation. The inventors found that >95% of the Dox added to the DNA did not release from the DNA during the ultrafiltration spin, indicating high retention of the drug even during a high speed spin (FIG. 4 (A)). The absorbance spectra of retentate and filtrate from this spin confirm that the absorbance maximum of retentate coincides with unfiltered Dox, whereas no such absorbance is detectable in the filtrate (FIG. 4 (B)). The retentate was then incubated with HerPBK10 and the resulting HerDox complex was separated from free components by high performance liquid chromatography (HPLC) size exclusion separation. Here the inventors show that the Dox absorbance mostly co-eluted with HerPBK10 (FIG. 5), as confirmed by SDS-PAGE of elution fractions (FIG. 5).

Example 3

HerDox is Highly Stable During Storage and in Serum

Figure 6:
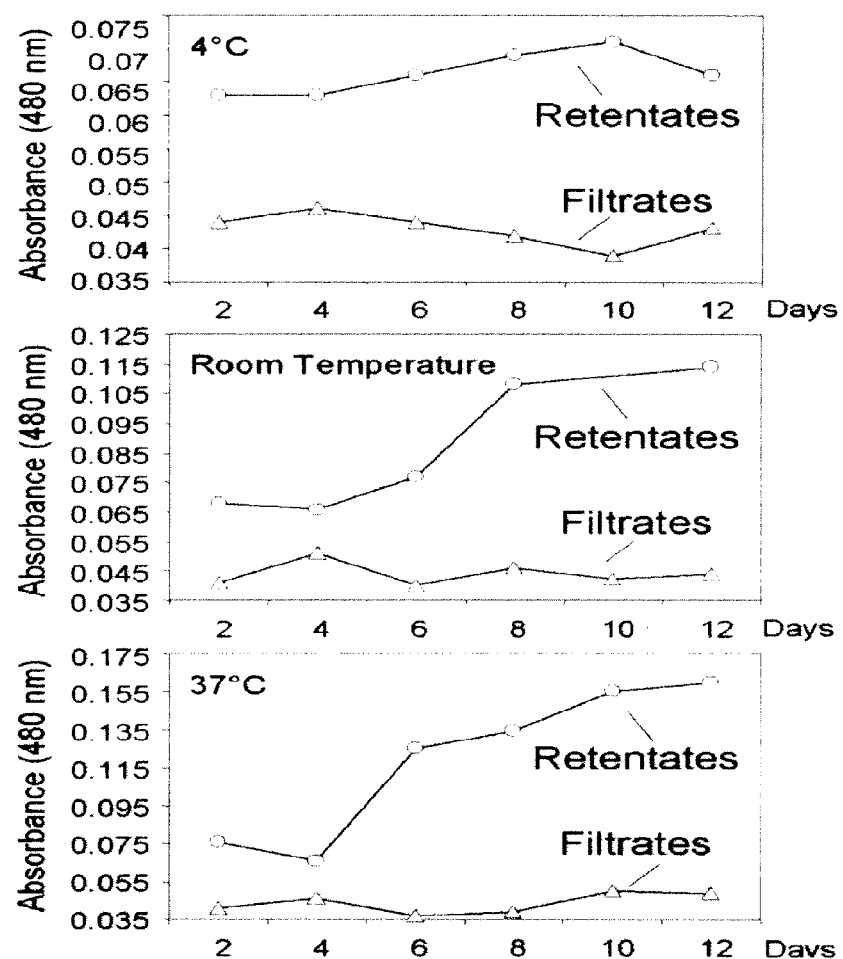
FIG. 6 (A)-(B) illustrates conjugate stability under different storage conditions, or in serum.
Figure 6:
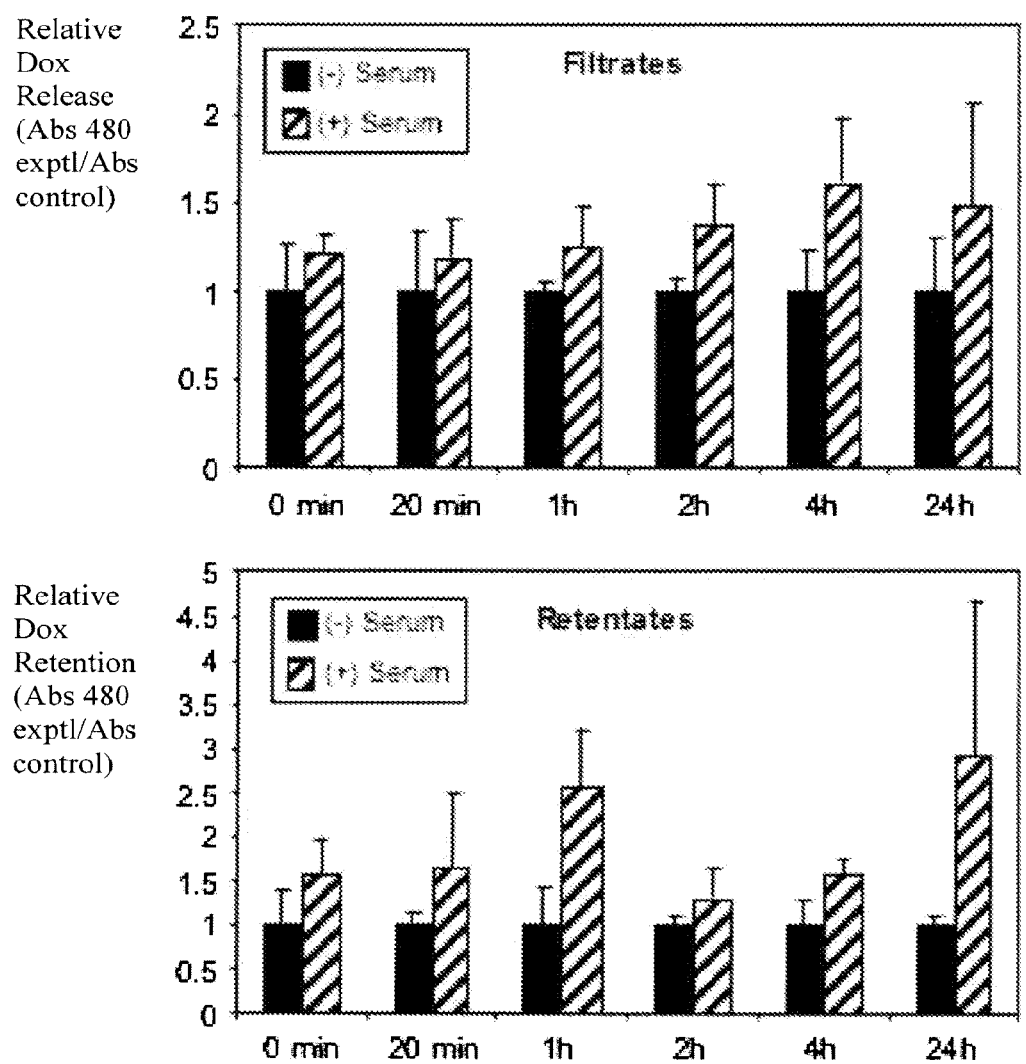

The inventors tested the stability of HerDox over 12 days under different storage temperatures: 4° C., room temperature, or 37° C. On each day, a sample underwent ultrafiltration, then filtrates and retentates were measured to determine whether any Dox was released from the complex. At 4° C., 100% of the product remained intact up to 12 days, and, interestingly, room temperature and 37° C. appeared to enhance the incorporation of the drug into the HerDox product (FIGS. 6 (A) and 6(B)). Altogether, these findings suggest that HerDox remains stable and does not release Dox after prolonged storage under different temperatures. The inventors also examined HerDox stability in serum-containing media at 37° C. HerDox immobilized on nickel sepharose (via the HerPBK10 histidine tag) was incubated at 37° C. in complete (i.e. 10% fetal bovine serum-containing) media (to mimic tissue culture conditions) for different time periods before the beads were pelleted and supernatants measured for Dox release. Dox retention in the conjugate was also assessed by eluting the conjugate from the beads at each time point. The inventors observed that the serum produced no significant release of Dox from the conjugate, which would be detected by an increase in Dox filtrate absorbance in the '(+) serum' samples (FIG. 6 (B), upper panel), and that the Dox was completely retained by the conjugate at each time point (FIG. 6 (B), lower panel).

Example 4

HerDox Produces Targeted Toxicity Whereas Dox Alone does not

Figure 7:
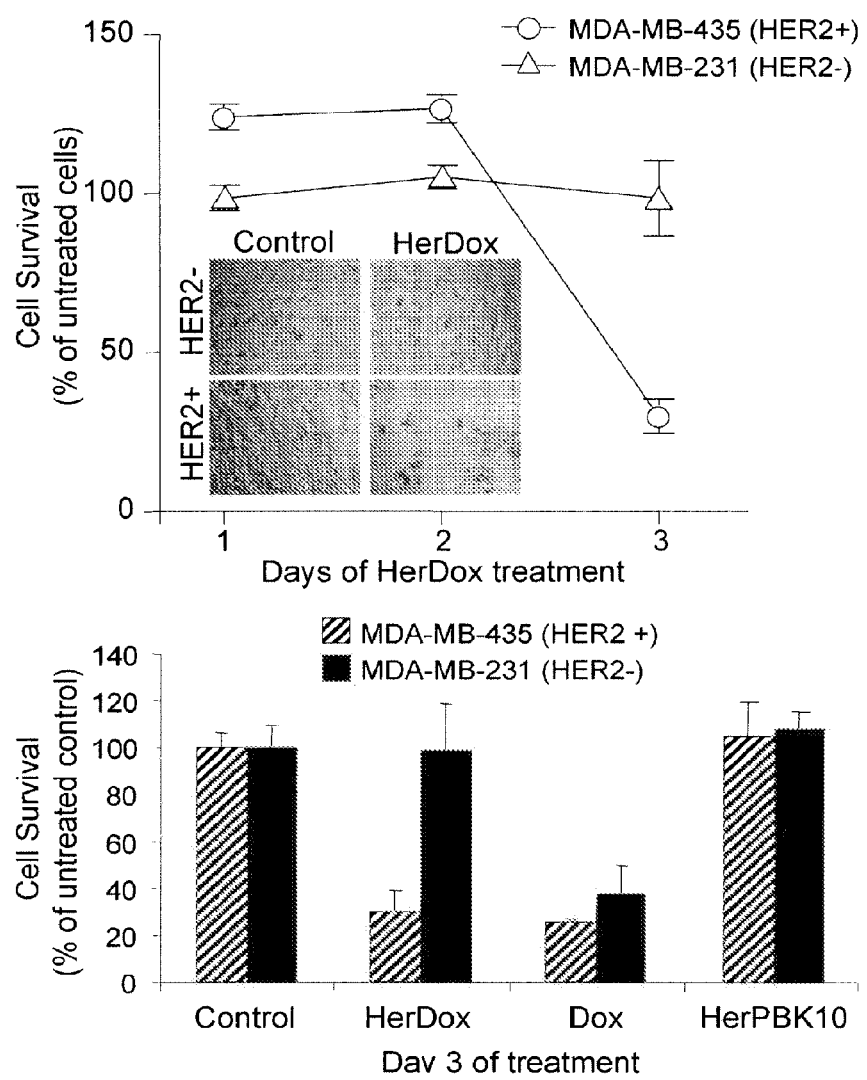
FIG. 7 illustrates targeted toxicity. Each cell line was exposed to HerDox (0.5 uM Dox conc), Dox alone (0.5 uM), or HerPBK10 alone for 4 h at 37° C. in complete (i.e. serum-containing) media, followed by aspiration to remove free conjugate, and addition of fresh medium while cells are grown continuously. Cell titer was determined by metabolic (i.e. MTT) assay.
Figure 8:
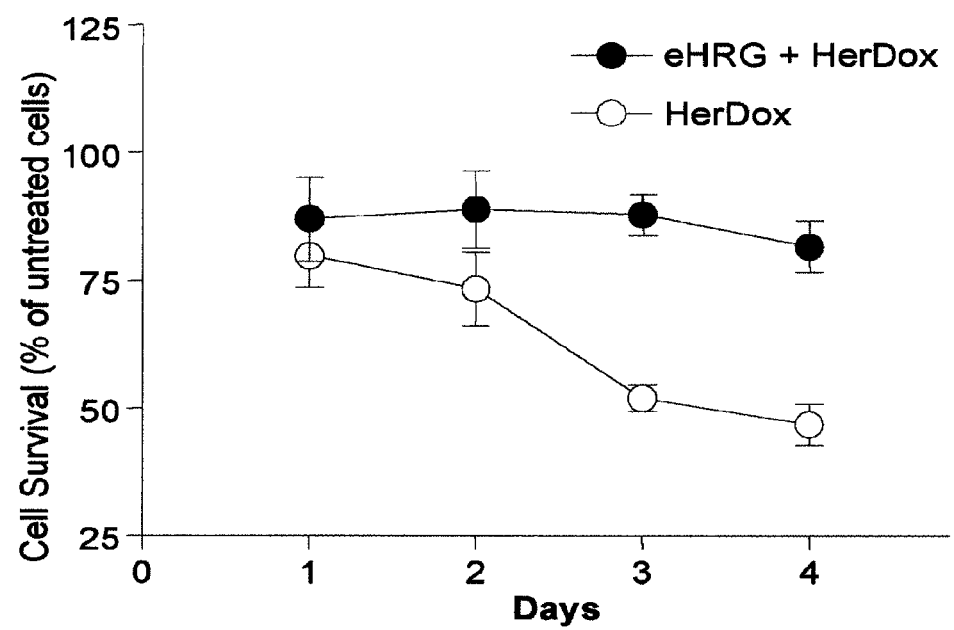
FIG. 8 illustrates receptor specificity. MDA-MB-435 (HER2+) cells were incubated with free ligand (eHRG) at 10× molar excess of HerDox for 1 h at 4° C. Media was aspirated to remove free eHRG and fresh media containing HerDox (0.5 uM) was added to cells. Cell survival was measured by MTT assay and represented as a % of relative untreated cell numbers.
Figure 9:
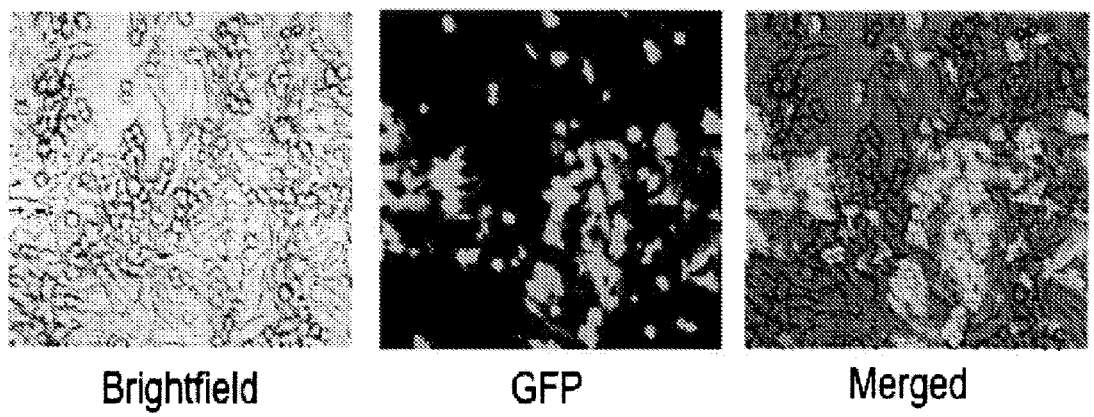
FIG. 9 (A)-(C) illustrates targeting in a mixed cell culture.
Figure 9:
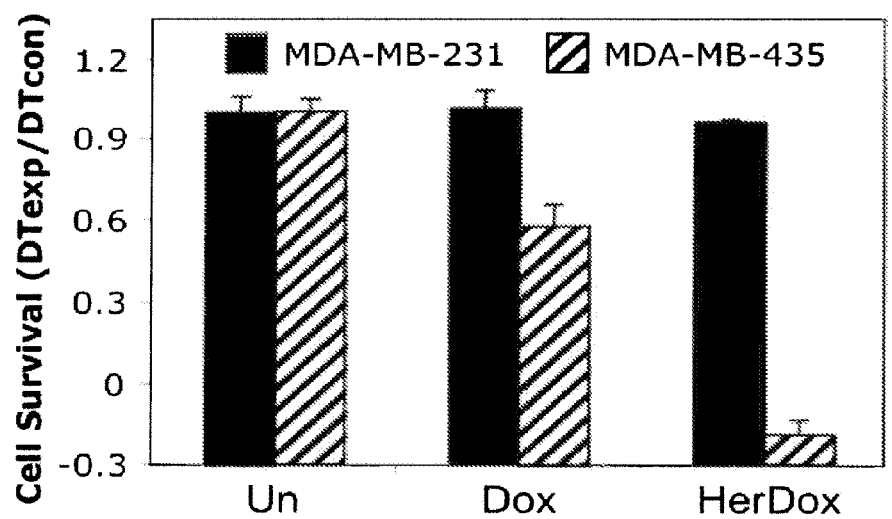
Figure 9:
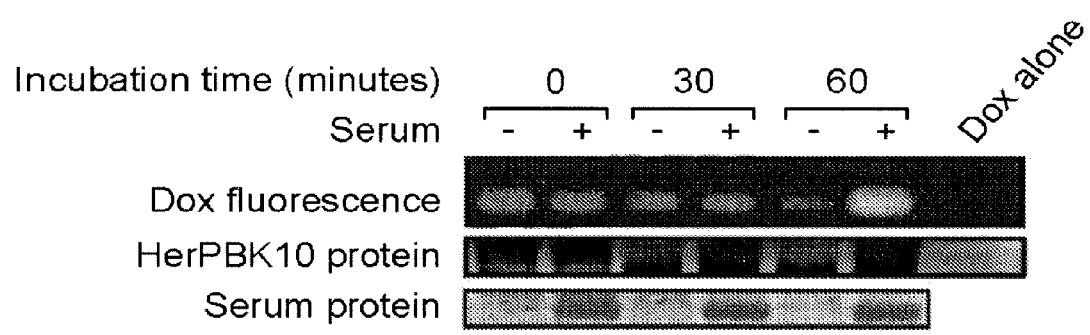

The inventors compared the effect of HerDox or Dox alone at equivalent dosages (0.5 uM with respect to Dox concentration) on HER2+ and HER2− breast cancer cells in separate dishes. By three days, HerDox reduced HER2+ cell numbers by over 75% whereas HER2− cell survival was unaffected (FIG. 7). Equivalent concentrations of Dox alone reduced both HER2+ and HER2− cells by the same order of magnitude (FIG. 7). These findings emphasize the importance of targeting by showing that the untargeted drug affects nontarget (i.e. HER2−) cells. Importantly, the protein carrier, HerPBK10, alone at the equivalent concentration of protein in HerDox (0.1 uM) had no effect on either cell line (FIG. 7), including a lack of proliferation induction. To test receptor targeting, the inventors used free heregulin ligand (Her or eHRG) as a competitive inhibitor. The free ligand completely inhibited cell killing by HerDox (FIG. 8), showing that HerDox bound and entered cells via the heregulin receptors. As a final in vitro challenge, the inventors tested whether HerDox induces toxicity specifically to HER2+ cells in a mixed culture of HER2+ and HER2− breast cancer cells. To do this, the inventors produced a HER2− cell line tagged with green fluorescent protein (GFP) for cell identification in the mixed culture (FIG. 9 (A)). The inventors found that HerDox nearly completely reduced non-GFP (HER2+) cell proliferation whereas GFP (HER2−) cell growth was not altered (FIG. 9 (B)). Altogether, these findings indicate that HerDox has the capacity to preferentially target toxicity to HER2+ cells. Importantly, all of these experiments were performed in complete (i.e. serum-containing) media, thus indicating that HerDox can target cells despite the presence of serum proteins. Moreover, the preferential cell killing of HER2+ cells in a mixed culture of HER2+ and HER2− cells implies that after death and lysis of the target cells, the Dox released into those cells is incapable of continuing to induce toxicity to HER2− cells. To further confirm the stability of HerDox in cell culture, HerDox was recovered from culture media in separate experiments at indicated time points and electrophoresed on an agarose gel, which was then illuminated by UV to detect Dox and stained with Coomassie blue to detect HerPBK10 protein (FIG. 9 (C)). As the gel does not retain free Dox, loss of Dox fluorescence over time would indicate that the conjugate released Dox. In serum-containing media, no such loss from HerDox is detectable. In serum-free conditions, it would appear that Dox fluorescence decreased by 1 h, however Coomassie blue staining shows that the decreased fluorescence is due to less sample loaded into the gel lane. Co-migration of HerPBK10 bands further verified that the conjugates remained intact in the cell media. Together with the serum-stability assay described earlier, these findings show that the conjugate remains intact during extended incubation in cell culture (which routinely contains at least 10% serum).

Example 5

GFP-Her Provides an Index of In Vivo Targeting

Figure 10:
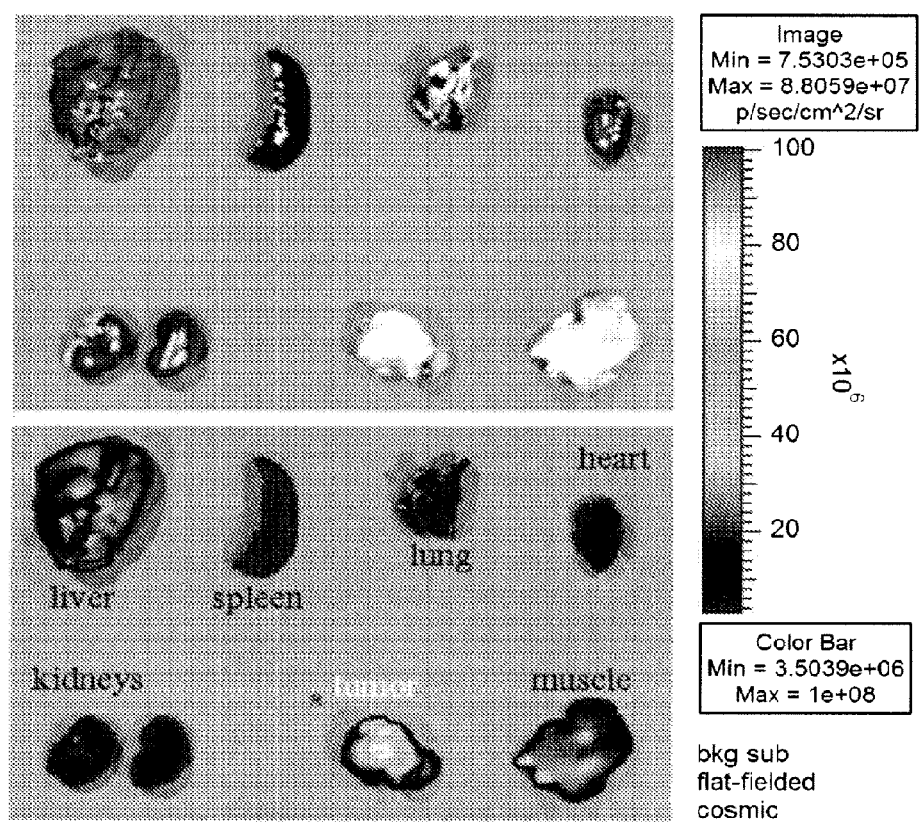
As illustrated in FIG. 10 (A), equal numbers of MDA-MB-435 and GFP(+) MDA-MB-231 cells were treated with Dox alone (0.5 uM), Her-Dox (containing 0.5 uM Dox), or HerPBK10 (1.2 ug/well, equivalent to HerPBK10 in HerDox). Wells were assayed for GFP fluorescence (to determine relative MDA-MB-231 number) and crystal violet staining (to determine total cell number).

To get a sense of the targeting ability of the ligand in vivo and establish an index of in vivo targeting, the inventors used a green fluorescent protein (GFP)-tagged ligand (GFP-Her. Importantly, this ligand is identical to the 'Her' domain of HerPBK10. We established HER2+ tumors in 6-8 week female nude mice via bilateral flank injections of MDA-MB-435 cells. When the tumors reached 250-300 mm$^3$ (~3-4 weeks after tumor cell implant), 3 nmoles of GFP-Her was injected via the tail vein. Mock injected mice received saline alone. Indicated tissues were harvested at 3.5 h after injection and imaged for GFP using a Xenogen IVIS three-dimensional small-animal in vivo imaging system (Xenogen, Alameda, Calif.). Preferential accumulation of GFP fluorescence was detected in the tumors over the other tissues (FIG. 10). Low to negligible levels of fluorescence were detected in the liver and muscle, while GFP fluorescence was undetectable in the other tissues, including the heart (FIG. 10). Tissues from mock-treated animals showed no fluorescence.

Example 6

HerDox Targets HER2+ Breast Cancer Cells In Vivo

Dox emits a red fluorescence upon appropriate wavelength excitation, which can be used to detect biodistribution after systemic delivery of HerDox. Mice bearing 4-week old tumors (~700-800 mm$^3$) received a single tail vein injection of Dox or HerDox (0.008 mg/mL with respect to Dox conc) and images of live mice captured in real time, or of organs/tissues harvested at ~3 h postinjection were acquired using a customized macro-illumination and detection system. Fluorescence was evident throughout the body at 10 min after HerDox injection, then quickly accumulated at the tumors by 20 min and remained detectable in the tumors up to 100 min after injection (FIG. 11 (A)). Tissues and tumors harvested at ~3 h after HerDox injection showed intense fluorescence in the tumors while substantially lower levels of fluorescence were detectable in the liver (FIG. 11 (B)). Some fluorescence was barely detectable in the kidneys while other tissues, including the heart, spleen, lungs, and skeletal muscle, did not exhibit any fluorescence. In contrast, tissues harvested from mice injected with the equivalent dose of Dox exhibited detectable fluorescence in the liver, tumor, and kidneys. Lower levels of fluorescence were also detectable in the lungs and skeletal muscle.

Figure 12:
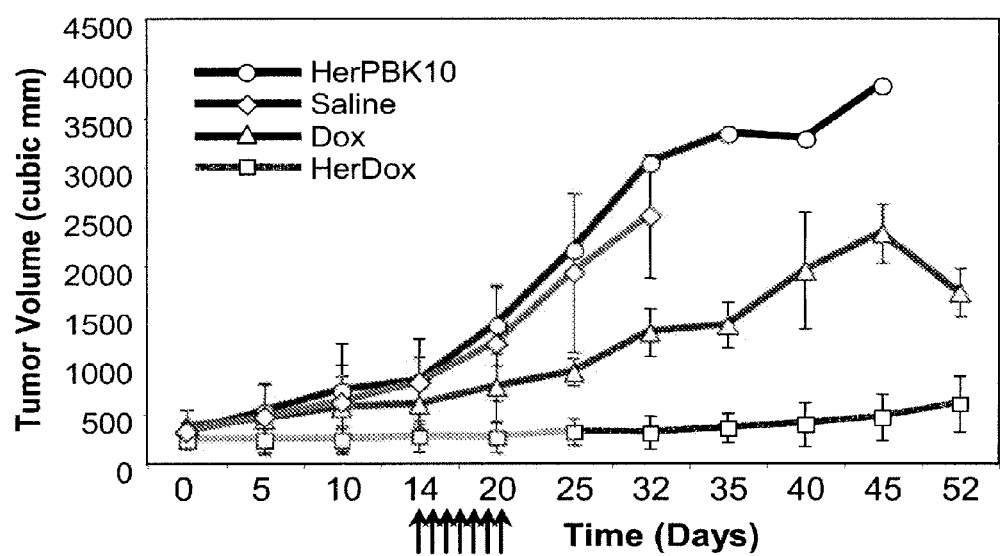
FIG. 12 (A)-(D) illustrates comparison of HerDox and Dox on (A) tumor growth, (B) animal weight, (C) cardiac tissue, and (D) cardiac function.
Figure 12:
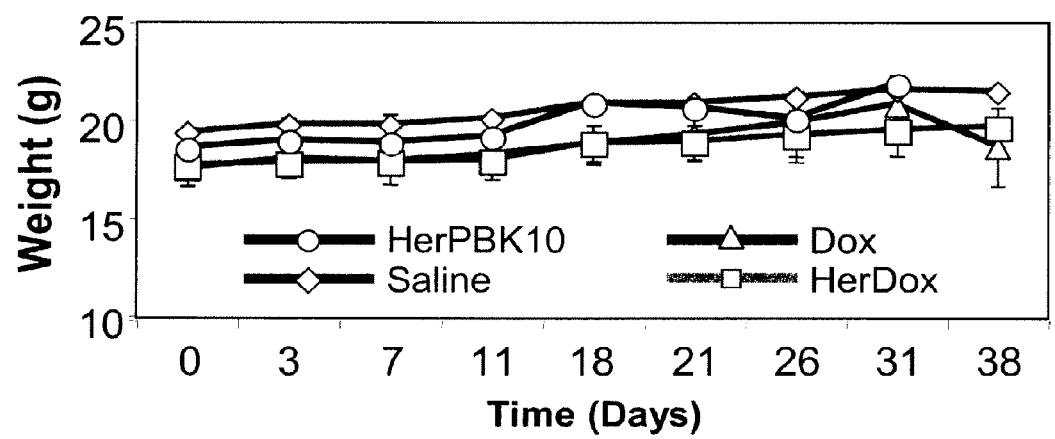
Figure 12:
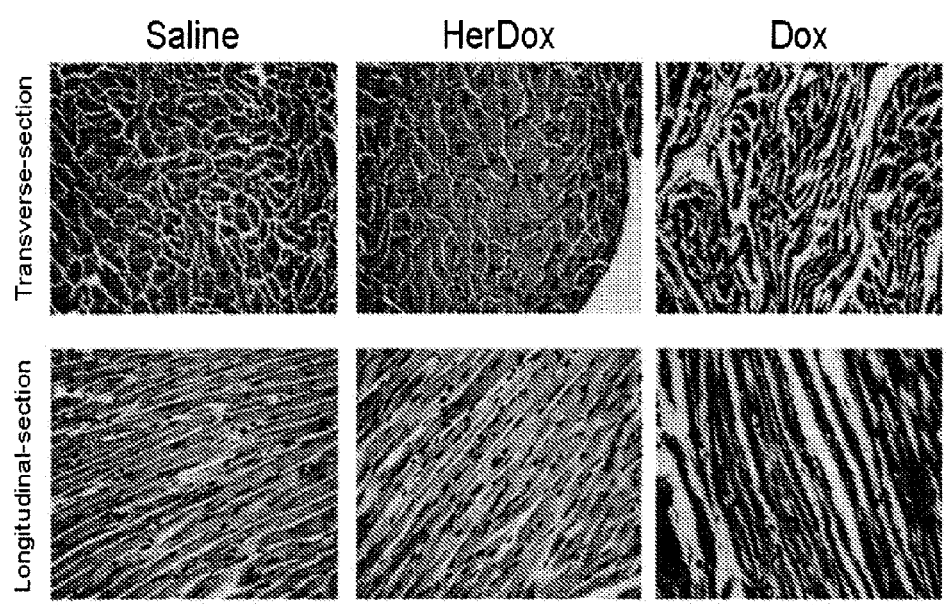
Figure 12:
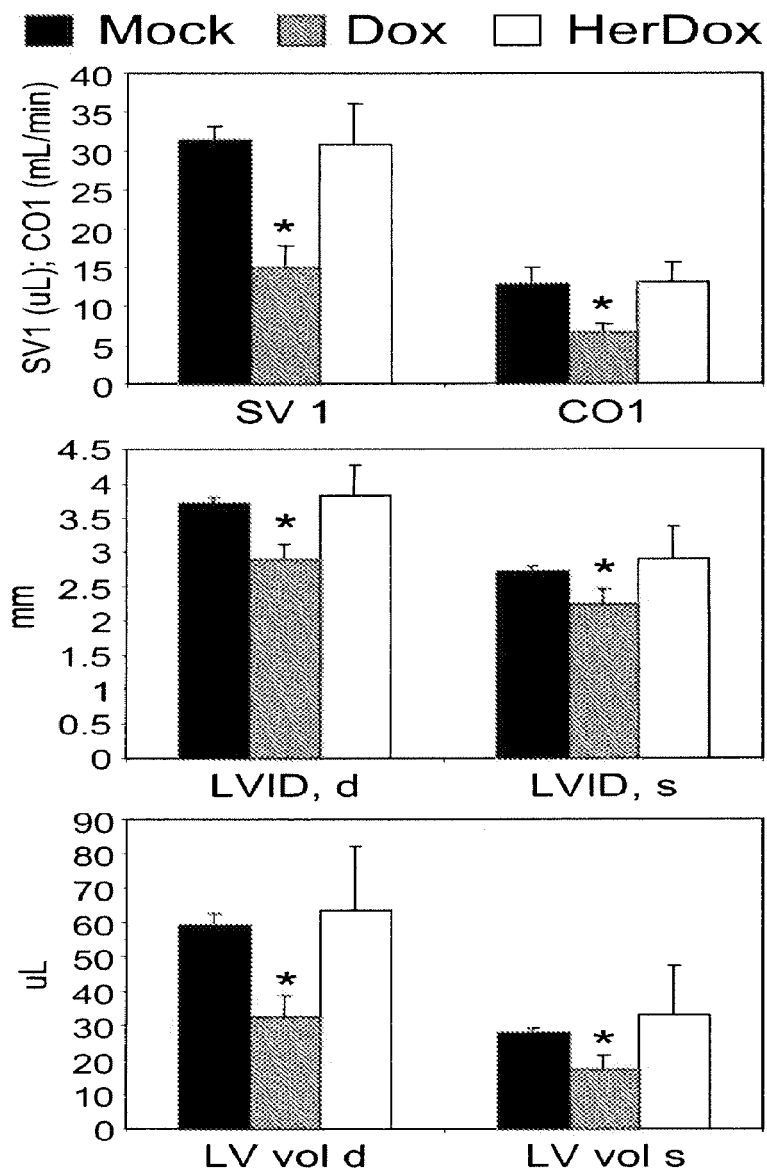

To assess in vivo tumor toxicity, mice bearing 3-4 week bilateral flank tumors began receiving daily tail vein injections of Dox or HerDox (0.004 mg/kg with respect to Dox conc), HerPBK10 alone (at equivalent protein concentration to HerDox) or saline for 7 consecutive days. Tumors were measured throughout tumor growth, beginning 2 weeks before tail vein injections, and show that while Dox slows tumor growth, HerDox essentially prevented tumor growth while HerPBK10 alone and saline had no effect (FIG. 12 (A)). No appreciable weight loss over time was observed in either treated or control mice (FIG. 12 (B)).

At 25 days following injections, tumors and organs were harvested and processed for histochemistry. It is established that Dox can induce acute and long-term cardiotoxicity, therefore, the inventors examined the hearts of mice treated with HerDox or Dox. Hearts from Dox treated mice appeared slightly enlarged and dilated relative to the hearts from HerDox and saline-treated mice (not shown), suggestive of the dilated cardiomyopathy associated with Dox toxicity. Myocardia from saline-treated mice exhibited normal cardiac morphology, whereas the those from Dox-treated mice exhibited focal degeneration, myofibrillar loss, increased cytosoplasmic vacuolization, and nuclear condensation or dissolution, typifying Dox-induced cardiotoxicity, whereas the myocardium from HerDox-treated mice, showed similar morphology to the saline-treated mice (FIG. 12 (C)). In agreement with these findings, echocardiograms obtained to assess cardiac function in treated mice show signs of Dox-induced dysfunction that is not detectable in HerDox-treated mice: whereas Dox induces modest to marked reductions in stroke volume, cardiac output, and left ventricular internal dimension and volume, HerDox has no effect on these measurements and appeared similar to mock (saline)-treated mice (FIG. 12(D)).

Figure 13:
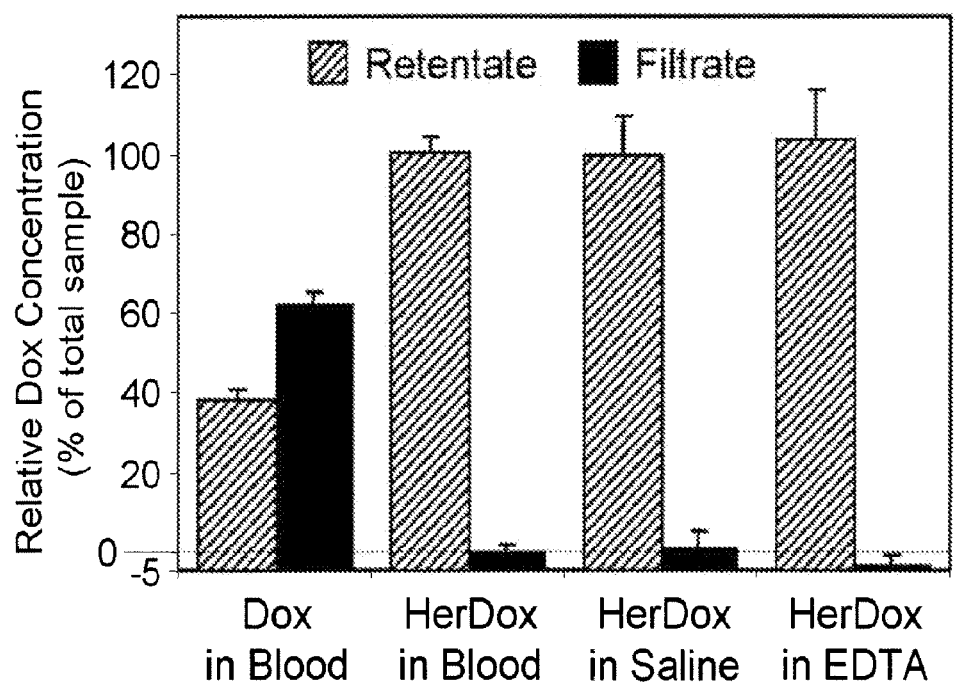
FIG. 13 illustrates stability in mouse whole blood. Freshly collected whole blood was processed by ultrafiltration through 10K MW cutoff membranes after up to 1 h incubation with HerDox or Dox at 37° C. As 0.5 mM EDTA was used as an anticoagulant, HerDox in EDTA alone (-blood) was processed in parallel. Bars represent fluorescence of retained (retentates) or released (filtrates) Dox as a percentage of the total fluorescence of each sample. Scale of Y-axis is adjusted to show presence of filtrate samples. N=3 per treatment.

To assess the feasibility of measuring in vivo stability, the inventors incubated HerDox (at 0.12 mg/mL final Dox conc) or free Dox at equivalent concentration in freshly collected whole blood from mice and incubated the mixtures at 37° C. up to 1 h. As the anticoagulant, 0.5 mM EDTA, was present in the blood collection, parallel samples were incubated at 37° C. in EDTA alone. Samples representing input HerDox (before incubation in blood) were incubated at 37° C. in HEPES-buffered saline. All samples were then centrifuged through 10K MW cutoff filters and Dox fluorescence measured in retentates and filtrates (SpectraMax M2 from Molecular Devices). The results show that there is no detectable loss of Dox from the conjugate, as evidenced by lack of detectable increase in filtrate fluorescence of HerDox, especially in comparison to the HerDox incubated in HBS or EDTA, or free Dox (FIG. 13). Likewise, there is no appreciable loss of Dox from HerDox retentates from samples incubated in blood compared to those incubated in saline or EDTA alone (FIG. 13). Taken together with the bioimaging results, these findings show that HerDox remains intact in blood and retains stability in vivo while in transit toward the tumor target.

Example 7

HerDox Mechanism: Dox Release in Cytoplasm & Accumulation in Nucleus

Figure 14:
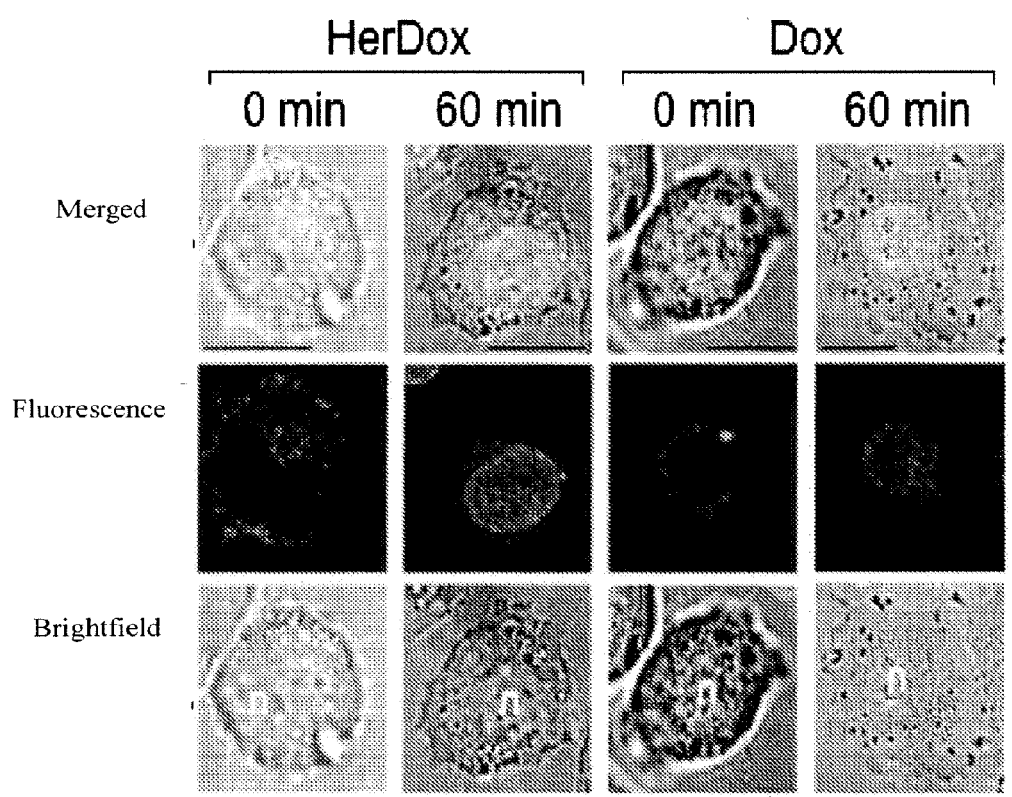
FIG. 14 (A)-(B) illustrates comparison of HerDox and Dox intracellular translocation and targets in live cells. MDA-MB-435 cells were incubated with HerDox or free Dox (0.5 uM) at 37° C. Live (unfixed) cells were imaged by brightfield and fluorescence, as depicted in FIG. 15 (A), or DIC and confocal fluorescence, as depicted in FIG. 14 (B), microscopy. Dox is indicated by red or magenta pseudo-color.
Figure 14:
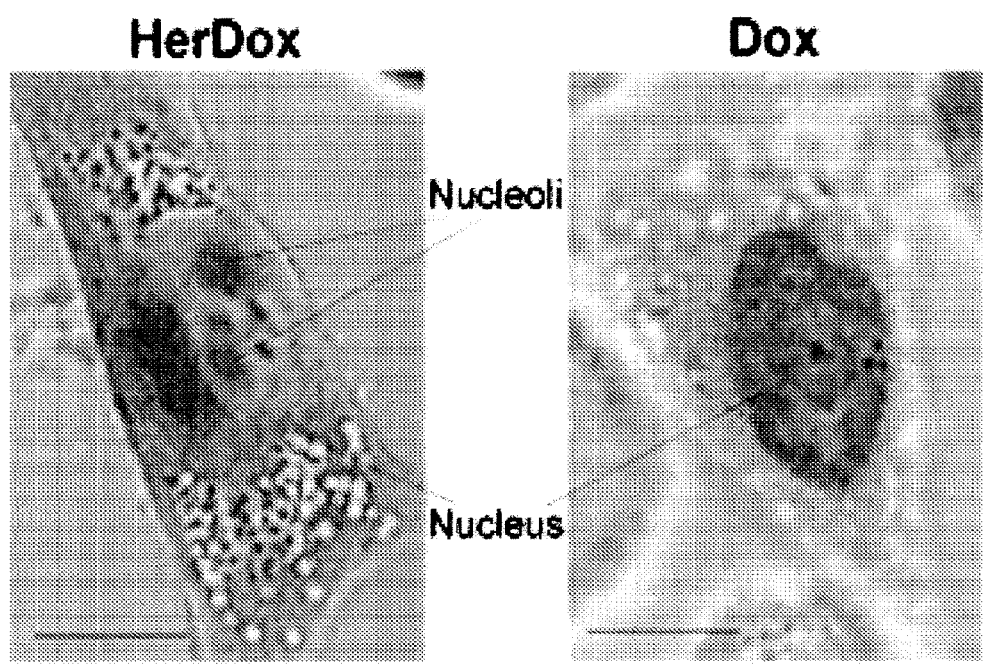

HerPBK10 alone does not induce cell death (FIG. 7), therefore it is the delivery of Dox into the cell that facilitates cell killing by HerDox. To understand the mechanism of HerDox-mediated tumor cell death, the inventors examined HER2+ cells microscopically after treatment with HerDox, using Dox fluorescence to detect intracellular location. Early after administration (at 0 min of uptake), HerDox appears mostly at the cell periphery, indicating that the conjugate is bound at the cell surface but not yet internalized (FIG. 14 (A)). In contrast, free Dox is already found inside the cell at the nuclear periphery (FIG. 14 (A)). At 60 min, when the majority of heregulin-targeted proteins have entered cells, Dox has accumulated in the nucleus, similar to free Dox (FIG. 14 (A)). These dynamics, in addition to earlier targeting results, support a receptor-mediated HerDox entry mechanism. Even the intranuclear pattern of Dox when delivered by HerPBK10 differs from free Dox. Whereas untargeted Dox accumulates in the cell nucleus, HerDox preferentially accumulates in nucleolar structures with some cytoplasmic fluorescence still visible (FIG. 14 (B)).

Figure 15:
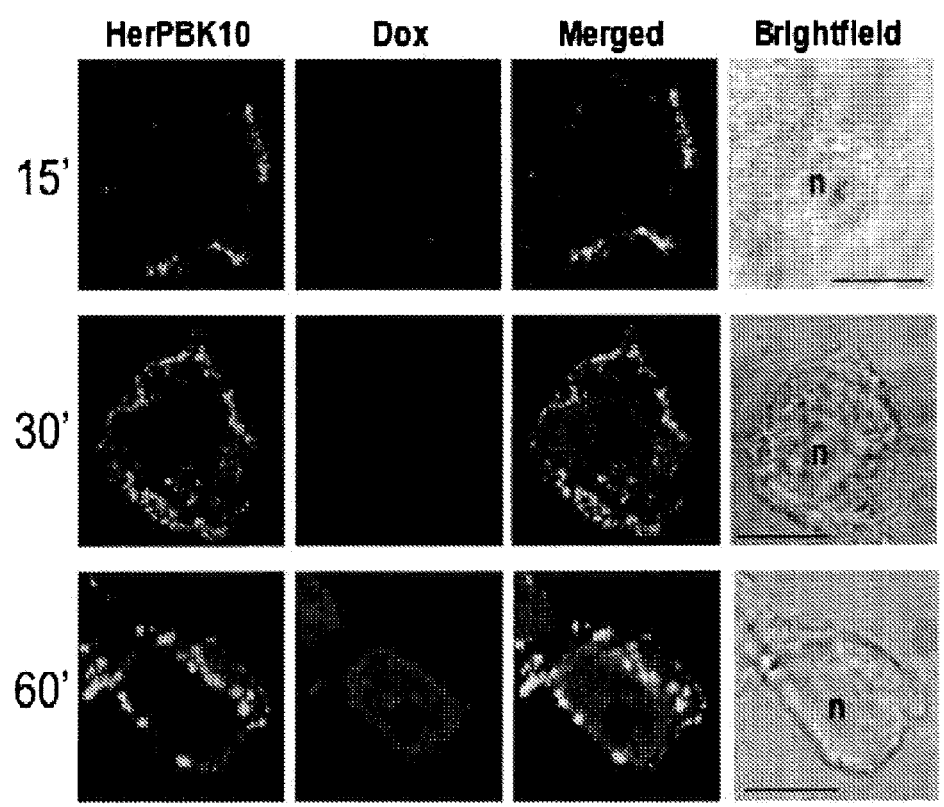
FIG. 15 illustrates HerDox trafficking in breast cancer cells. Cells incubated with HerDox at 37° C. were fixed at the indicated time points and processed for immunofluorescence using an antibody against HerPBK10. Images were captured using confocal microscopy under fluorescence and brightfield. Green, HerPBK10; Red, Dox. n, nucleus Bar, ~8 microns.

To determine whether Dox remains attached to HerPBK10 during uptake, the inventors used immuno-fluorescence against HerPBK10. At 15 min of uptake, HerPBK10 mostly colocalizes with Dox, suggesting that a substantial population of HerDox is still intact, though some nuclear accumulation of Dox is already visible (FIG. 15). At 30 and 60 min, increasing levels of Dox accumulate in the nucleus while the majority of HerPBK10 remains in the cytoplasm (FIG. 15). In fixed cells, nucleolar accumulation was not detectable as in the live cells (FIG. 14 (B)). Altogether, these findings show that HerPBK10 delivers Dox into the cell and releases the Dox intracellularly where it undergoes nuclear accumulation, consistent with the mechanism of delivery (FIG. 11 (B)).

Example 8

Human Serum has No Notable Effect on Cell Binding

Figure 16:
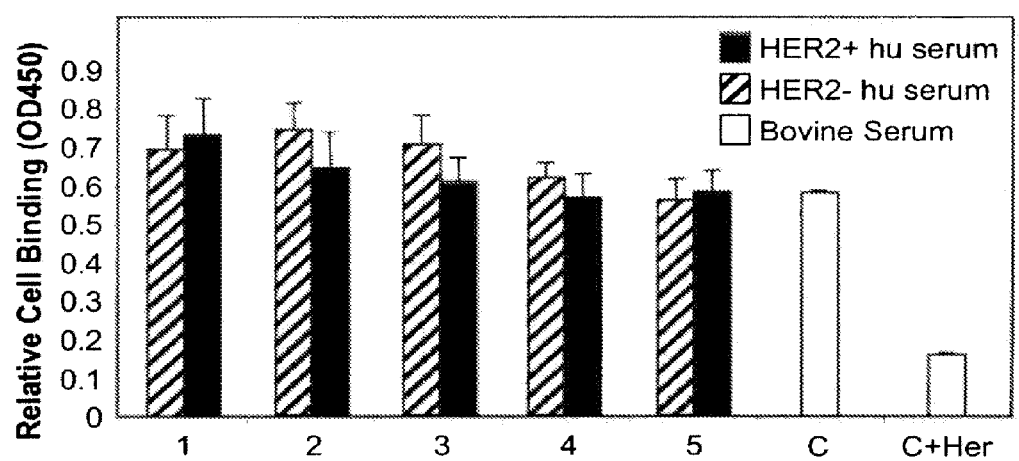
FIG. 16 illustrates HerPBK10 binding to MDA-MB-435 cells in human serum from HER2+ or HER2− breast cancer patients. Cells were treated with HerPBK10 (1.2 ug/well) in media containing human serum from each of 5 HER2+ breast cancer patients or age matched HER2− controls, both obtained pre-chemotherapy treatment. Cells were processed for ELISA using an antibody directed at HerPBK10. Control (C) wells receiving HerPBK10 in media containing bovine serum without or with 100× molar excess competitive ligand inhibitor (+Her) are indicated by open bars. Patient sera were provided by the WCRI tissue bank at Cedars-Sinai Medical Center. N=3 wells per treatment.

To determine whether HerPBK10 can compete with circulating ligand that may be present in serum, the inventors tested HerPBK10 binding to HER2+ breast cancer cells in human serum obtained from HER2+ patients. The Women's Cancer Research Institute at Cedars-Sinai occasionally acquires limited quantities of patient serum, of which sera from HER2+ patients comprises an even smaller minority. Notably, the human serum used here is the actual fraction of serum and associated proteins isolated from collected whole blood of HER2+ and age-matched HER2− patients. Earlier experiments demonstrate that HerDox binds cell targets in complete medium containing 10% bovine serum, and that this binding is competitively inhibited by excess free ligand. Here, the inventors replaced the bovine serum in the routine culturing media with the human serum obtained from the acquired patient samples to assess whether the human serum, especially from HER2+ patients, inhibits cell binding. The inventors ensured that cells received considerable exposure to the human sera (2 hours, which provides ample time for receptor binding of any circulating ligand) prior to treatment. Head-to-head comparisons of cell binding in serum from either HER2+ patients, HER2− patients, or bovine serum show no significant differences (FIG. 16), indicating that the human sera tested here did not interfere with HerPBK10 binding to target cells. Competitive inhibition with 100× heregulin ligand (+Her) confirms that the control binding activity is specific to heregulin receptors.

Example 9

HER Subunit Levels and Cytoxicity on Proposed Cell Types

Figure 17:
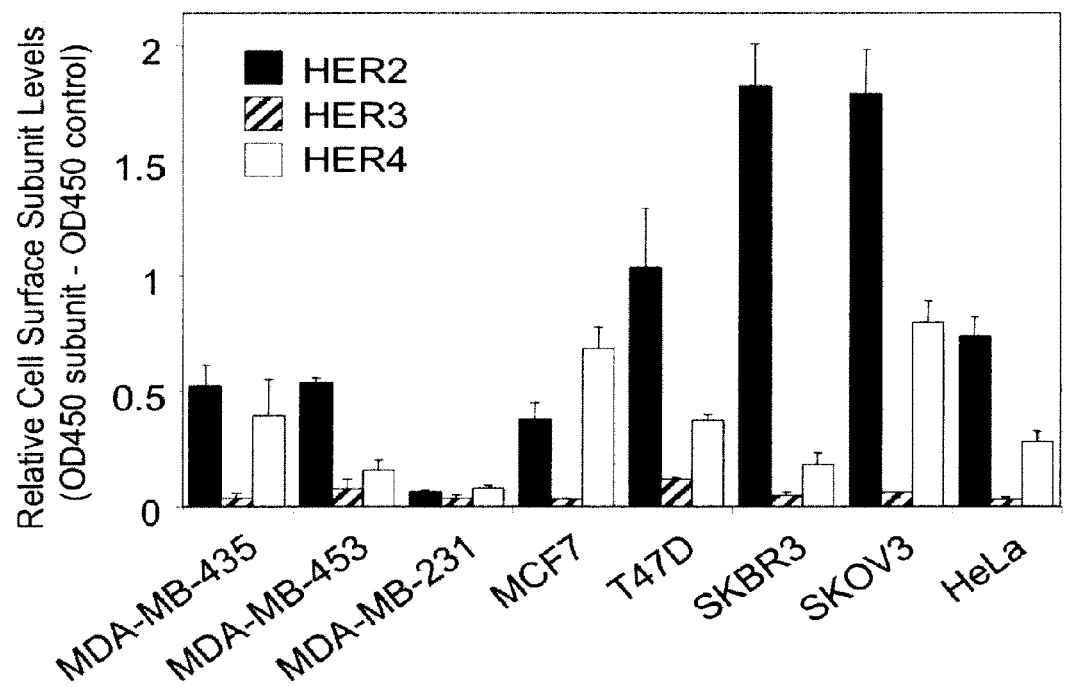
FIG. 17 (A)-(B) illustrates relative cell surface HER subunit levels and cytotoxicity on cell types.
Figure 17:
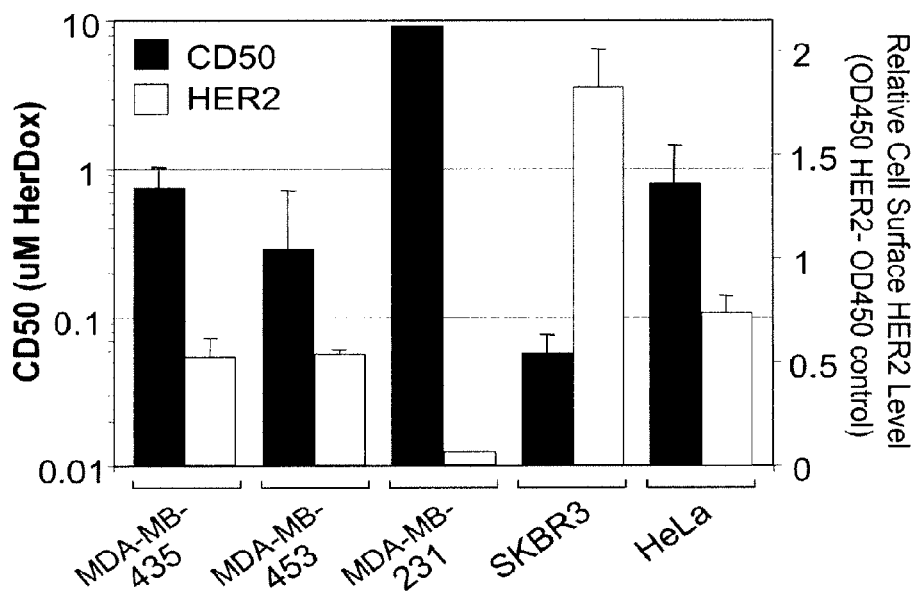

The inventors measured cell surface levels of HER subunits on various cell lines and types described herein, as previously described levels may not reflect the actual levels in the available cells used. The inventors acquired the indicated cell lines from ATCC and the NIH/NCI and profiled these with respect to HER subunit levels (FIG. 17 (A)). To assess whether HerDox induces toxicity in accordance to HER2 levels, the inventors selected lines displaying HER2 at relatively high (SKBR3), moderate (MDA-MB-435, MDA-MB-453, HeLa), and low to undetectable (MDA-MB-231) levels, and performed cytotoxicity dose curves. The inventors observed that HerDox CD50 inversely correlates with cell surface HER2 level on these selected lines: the cell line displaying relatively high HER2 shows a relatively higher sensitivity to HerDox whereas the cell line displaying low HER2 exhibits low sensitivity, and the lines displaying intermediate HER2 levels likewise exhibit intermediate sensitivities (FIG. 17 (B); CD50 is shown on a log scale).

TABLE 1

Cytotoxicity on cell lines
Example 10

| CELL LINE | HER2* | EC50** (uM HerDox) |
|---|---|---|
| MDA-MB-231 | 0.06 ± 0.006 | 7.2e5 ± 0.11 |
| MDA-MB-435 | 0.52 ± 0.08 | 0.74 ± 0.07 |
| T47D | 1.03 ± 0.26 | 0.64 ± 0.04 |
| SKOV3 | 1.79 ± 0.19 | 0.18 ± 0.03 |

*Relative cell surface level (mean ± 1SD) as determined ELISA. N = 3 wells.
**Concentration (mean ± 1SD) yielding 50% reduction in cell survival, as determined by nonlinear regression analyses of HerDox dose curves. N = 3 treated wells per dose.

Example 11

Optimization of HerPBK10

Figure 18:
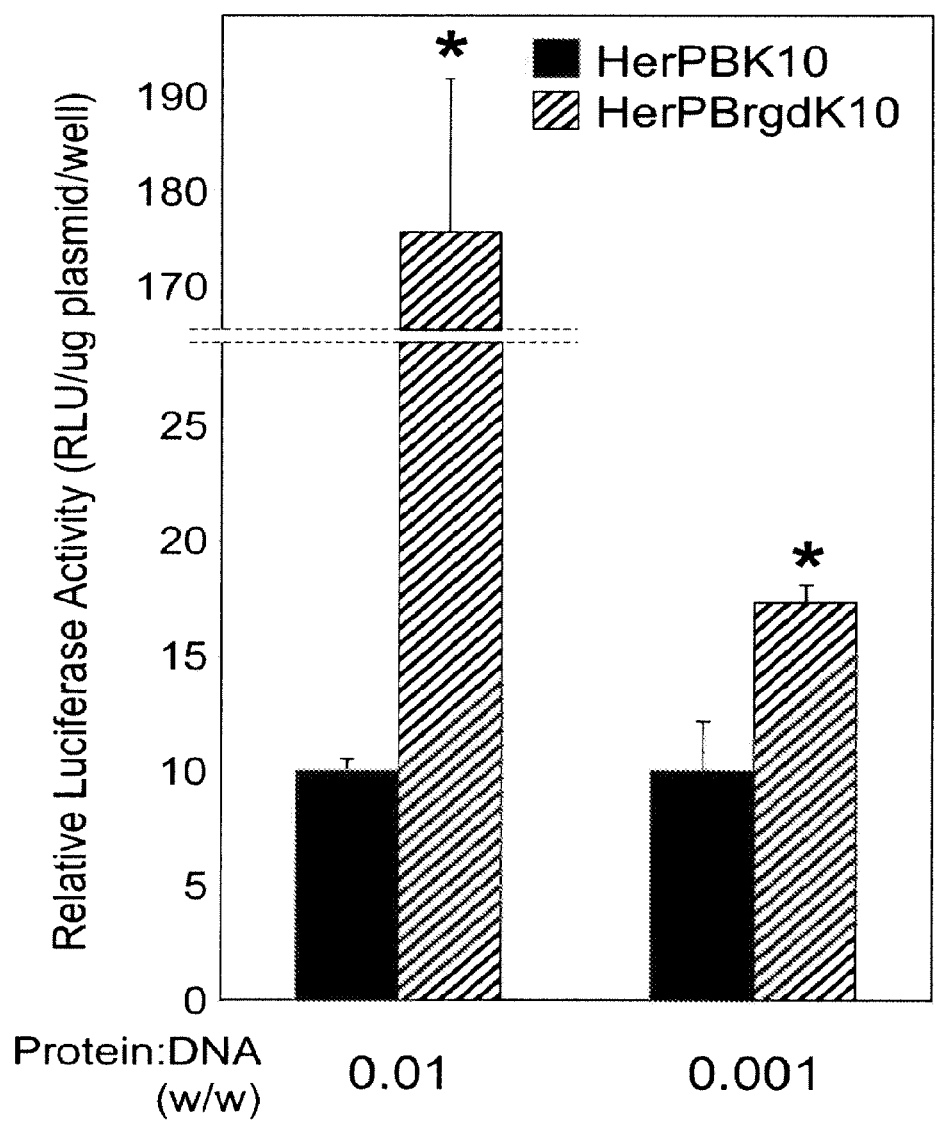
FIG. 18 illustrates optimization of HerPBK10. The delivery capacity of the modified protein, HerPBrgdK10 was tested in the context of a nonviral gene transfer complex, and delivery efficiency assessed by transgene (luciferase) expression in MDA-MB-453 human breast cancer cells. *, $P<0.005$ compared to equivalent concentration of HerPBK10, as determined by 2-tailed T test. The figure demonstrates that the invention is in no way limited to HerPBK10 as various mutations may be introduced that will improve targeting, receptor binding, cell entry and/or intracellular trafficking of the protein.

As the HerPBK10 protein originates from the adenovirus penton base protein, whose natural binding targets are alpha-v integrins, the inventors assessed whether mutation of the Arg-Gly-Asp (RGD) integrin binding motif improves the capacity of the protein to deliver cargo into cells. While previous studies indicate that appendage of the heregulin receptor binding ligand to the penton base redirects it nearly exclusively to heregulin receptors (as demonstrated by competitive inhibition assay), it is possible that HerPBK10 may still co-opt integrin receptors that may redirect the protein to a different intracellular route or compete for binding sites on the protein itself. Rendering the RGD motif to EGD by point mutation disables integrin binding. Therefore, the mutant protein, HerPBrgdK10 was produced bearing this mutation, and tested for gene delivery in comparison to parental HerPBK10. At equivalent protein concentrations, HerPBrgdK10 exhibited moderate (~1.8-fold) to dramatic (~18-fold) enhancement of gene transfer (FIG. 18), which may be reflective of enhanced receptor binding or post-binding activities.

Example 12

DNA Constructs

The inventors used a common 5' oligonucleotide primer containing the sequence 5'-ATCGAAGGATCCATGCGGCGCGCGGCGATGTAT-3' (SEQ. ID. NO.: 12) to amplify both wild-type and lysine-tagged penton sequences from a pJM17 adenoviral genome template. The sequences of the 3' primers are PB: 5'-GCATCAGAATTCTCAAAAAGTGCGGCTCGATAG-3' (SEQ. ID. NO.: 1) and PBK10 5'-CATGAATTCA(TTT)10AAAAGTGCGGCTCGATAGGA-3' (SEQ. ID. NO.: 2). A BamHI restriction site was introduced in the 5' primer and an EcoRI restriction site was introduced in the 3' primers for in-frame insertion of both the wild-type and lysine-tagged pentons into the pRSET-A bacterial expression plasmid (Invitrogen, Carlsbad, Calif., USA). This plasmid expresses the recombinant protein as an N-terminally histidine-tagged fusion for affinity purification by nickel chelate affinity chromatography.

Polymerase chain reaction (PCR) amplification was used to add a sequence encoding a short polyglycine linker to the amino (N)-terminus of PBK10. The sequence encoding the linker contains a SacII restriction site for additional cloning. The heregulin targeting ligand was produced by PCR amplification of the epidermal growth factor (EGF)-like domain of the heregulin gene29 using a 5' oligonucleotide primer containing a BamHI site and a 3' primer containing a SacII site for cloning in-frame with PBK10. The targeting ligand was added to the lysinetagged construct to create HerPBK10 by ligating the PCR product just N-terminal to PBK10. Construction of Her and GFP-Her have been previously described (Medina-Kauwe L K, et al., *BioTechniques* 2000, 29: 602-609). HerK10 was created by PCR amplification of the Her construct using a 5' Her primer (Medina-Kauwe L K, et al., *BioTechniques* 2000, 29: 602-609) and a 3' oligo-nucleotide primer containing the sequence 5'-ATGAATTCA (TTT)10AGATCTACTTCCACCACTTCCACC-3' (SEQ. ID. NO.: 3).

Example 13

DS-Oligo Length does not Affect Dox Incorporation into the Targeted Complex

Figure 19:
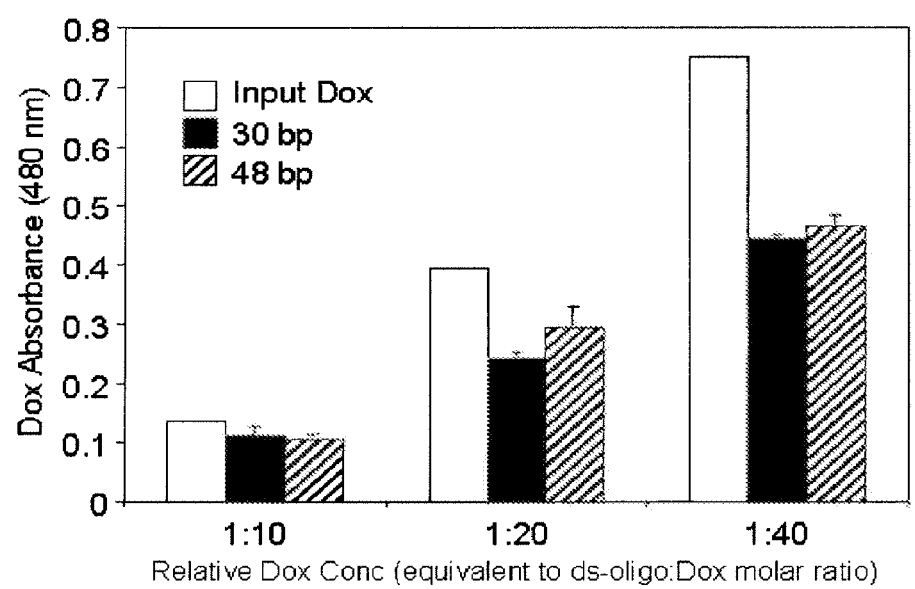
FIG. 19 illustrates a graph demonstrating that DS-oligo length does not affect Dox incorporation into the targeted complex. The graph demonstrates that there is no appreciable difference in Dox incorporation using either 30 or 48 base pair duplexes.

Ds-oligo duplexes were formed from complimentary 30 bp sequences, LLAA-5 (SEQ. ID. NO.: 6) and LLAA-3 (SEQ. ID. NO.: 7) or 48 bp sequences, BglIIHis-5 (SEQ. ID. NO.: 8) and BglIIHis-3 (SEQ. ID. NO.: 9). Dox was added to each set of annealed duplexes at either 1:10, 1:20, or 1:40 molar ratio duplex:Dox (at a final Dox concentration of either 20, 40, or 80 uM) in 10 mM Tris/HCl buffer, pH 8.0, for 30 minutes at room temperature. The mixtures were then centrifuged through ultrafiltration membranes (Microcon Ultracel YM10; Millipore) at 10,000×g to separate free Dox from incorporated Dox. Retentates and filtrates were collected separately, and absorbances of each measured at 480 nm using a SpectraMax M2 plate reader (Molecular Devices). The results (FIG. 19) show that there is no appreciable difference in Dox incorporation using either 30 or 48 bp duplexes.

Example 14

HerDox is Toxic to Glioma Cells

Figure 20:
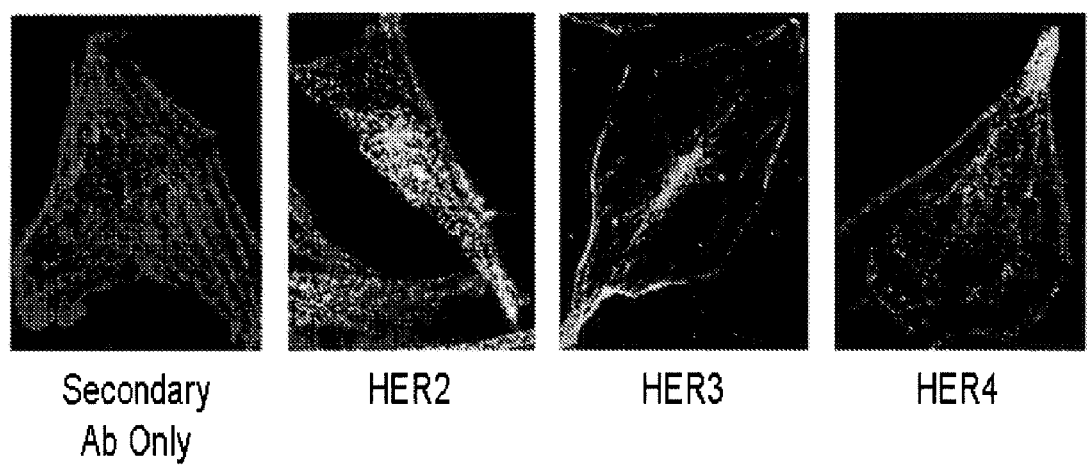
FIG. 20 (A)-(B) illustrates HerDox is toxic to glioma cells.
Figure 20:
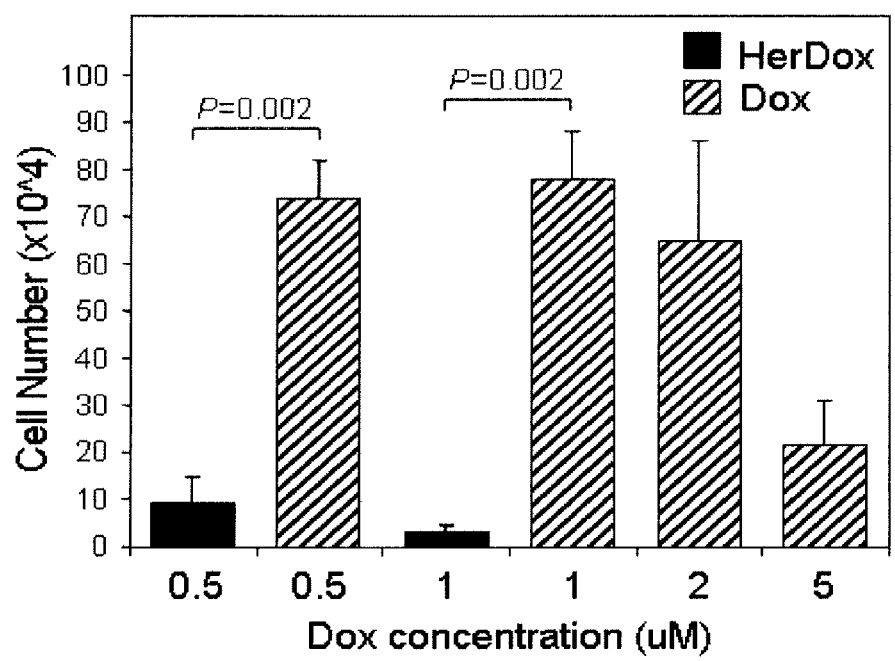

U251 human glioma cells were assessed for HER subunit levels by non-permeabilizing immunohistochemistry and found to display relatively marked levels of cell surface HER2, HER3, and HER4 (FIG. 20 (A)).

U251 cells growing in dishes were incubated with either HerDox or Dox (at either 0.5 uM or 1 uM) in the culture medium for 4 hours at 37° C., 5% C02, after which fresh complete medium was added to increase the final culture volume approximately four-fold, and the cells maintained at 37° C., 5% C02 for four days. Cells were trypsinized and counted on the last day.

The inventors' results show that HerDox exhibits 8-10 times more toxicity to U251 cells than the equivalent concentration of Dox, and likewise 10× less HerDox elicits the same toxicity as Dox (FIG. 20 (B)).

Example 15

Summary

These studies indicate that a stable non-covalent conjugate can assemble and direct a well-established chemotherapy drug to target cells in serum. Delivery is mediated via the heregulin receptor, as free ligand competitively inhibits delivery. Importantly, the inventors have demonstrated that toxicity can be targeted to HER2+ cells in a mixed cell culture and in vivo. These studies show that the carrier protein, HerPBK10, is capable of mediating targeted toxicity and that drug conjugates non-covalently linked to this carrier can be assembled and delivered with apparently little to no premature release or nonspecific toxicity.

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive. One skilled in the art will recognize many methods and materials similar or equivalent to those described herein, which could be used in the practice of the present invention. Indeed, the present invention is in no way limited to the methods and materials described. For example, various agents may be delivered in conjunction with embodiments described herein and the invention should not be merely limited to Dox or chemotherapy agents. Similarly, various motifs could be used interchangeably with or in addition to those described herein and the invention should not be construed as limited to only polylysine motifs and/or RGD motifs. Finally, as recognized by one of skill in the art, the invention can be applied to any number of conditions, disorders and/or diseases where it is advantageous to target delivery of an agent to a cell and/or cell nucleus and the present invention should not be construed in any way as limited to the treatment of breast cancer.

The invention claimed is:

1. A method of treating a disease in an individual, comprising:
   administering a therapeutically effective amount of a drug delivery molecule to the individual, the drug delivery molecule comprising:
   a polypeptide sequence adapted to target and penetrate a type of cell,
   a nucleic acid sequence bound to the polypeptide sequence via electrostatic interactions, and
   a chemical agent non-covalently linked to the nucleic acid sequence.

2. The method of claim 1, wherein the disease is breast cancer.

3. The method of claim 1, wherein the chemical agent is a chemotherapeutic agent.

4. The method of claim 1, wherein the chemical agent is doxorubicin.

5. The method of claim 1, wherein the polypeptide sequence comprises a targeting ligand, an endosomolytic domain, or a polylysine motif.

6. The method of claim 1, wherein the individual is a human.

7. The method of claim 1, wherein the type of cell is a glioma cell.

8. The method of claim 1, wherein the polypeptide sequence comprises PBK10.

9. The method of claim 1, wherein the disease is metastatic cancer.

10. The method of claim 1, wherein the disease is cancer.

11. The method of claim 1, wherein the type of cell is a breast cancer cell.

12. The method of claim 1, wherein the type of cell is a HER2+ breast cancer cell.

13. The method of claim 1, wherein the polypeptide sequence comprises a targeting ligand.

14. The method of claim 13, wherein the targeting ligand comprises Her.

15. The method of claim 1, wherein the polypeptide sequence comprises a penton base or a variant thereof.

16. The method of claim 15, wherein the penton base comprises an EGD motif in place of an RGD motif.

17. The method of claim 15, wherein the polypeptide sequence further comprises a targeting ligand.

18. The method of claim 17, wherein the targeting ligand comprises Her.

19. The method of claim 1, wherein the polypeptide sequence comprises a polylysine motif.

20. The method of claim 19, wherein the polypeptide sequence further comprises a penton base or a variant thereof.

21. The method of claim 20, wherein the polypeptide sequence further comprises a targeting ligand.

22. The method of claim 21, wherein the targeting ligand comprises Her.

23. The method of claim 1, wherein the nucleic acid sequence comprises a sequence according to SEQ ID NO: 6, SEQ ID NO: 7, SEQ ID NO: 8, or SEQ ID NO: 9.

24. The method of claim 1, wherein the nucleic acid sequence is a double stranded nucleic acid sequence comprising a first nucleic acid molecule having a sequence according to SEQ ID NO: 6, and a second nucleic acid molecule having a sequence according to SEQ ID NO: 7.

25. The method of claim 1, wherein the chemical agent intercalates with the nucleic acid sequence.

26. The method of claim 1, wherein the polypeptide sequence comprises a targeting ligand, a penton base or a variant thereof, and a polylysine motif.

27. The method of claim 1, wherein the polypeptide sequence comprises HerPBK10.

28. The method of claim 27, wherein the nucleic acid sequence is a double-stranded nucleic acid sequence.

29. The method of claim 28, wherein the chemical agent comprises doxorubicin.

30. The method of claim 29, wherein the doxorubicin intercalates with the double stranded nucleic acid sequence.

31. The method of claim 28, wherein the double-stranded nucleic acid sequence comprises a first nucleic acid molecule having a sequence according to SEQ ID NO: 6, and a second nucleic acid molecule having a sequence according to SEQ ID NO: 7.

32. The method of claim 31, wherein the chemical agent comprises doxorubicin.

33. The method of claim 32, wherein the doxorubicin intercalates with the double stranded nucleic acid sequence.

* * * * *